(12) United States Patent  (10) Patent No.: US 7,608,742 B2
Friedrich et al.  (45) Date of Patent: Oct. 27, 2009

(54) DIARYLPHENOXY ALUMINUM COMPOUNDS

(75) Inventors: Marko Friedrich, Lorsch (DE); Klaus Ebel, Lampertheim (DE); Norbert Götz, Worms (DE); Wolfgang Krause, Brühl-Rohrhof (DE); Christian Zahm, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 232 days.

(21) Appl. No.: 11/817,468

(22) PCT Filed: Mar. 3, 2006

(86) PCT No.: PCT/EP2006/060416

§ 371 (c)(1),
(2), (4) Date: Aug. 30, 2007

(87) PCT Pub. No.: WO2006/092433

PCT Pub. Date: Sep. 8, 2006

(65) Prior Publication Data

US 2008/0167504 A1  Jul. 10, 2008

(30) Foreign Application Priority Data

Mar. 3, 2005  (DE) ........................ 10 2005 010 329
Sep. 16, 2005  (DE) ........................ 10 2005 044 518

(51) Int. Cl.
C07C 35/08  (2006.01)
C07F 5/06  (2006.01)

(52) U.S. Cl. .................. 568/828; 568/829; 556/27; 556/181

(58) Field of Classification Search .................. 568/828, 568/829; 556/27, 181
See application file for complete search history.

(56) References Cited

U.S. PATENT DOCUMENTS 3,123,647 A   3/1964  Duennenberger et al.
3,739,035 A   6/1973  Webb et al.

FOREIGN PATENT DOCUMENTS

DE   2534558 A1   2/1977
EP   1053974 A1   11/2000
JP   9278817      10/1997

OTHER PUBLICATIONS

Ito, H., et al., "Chiral molecular recognition by aluminum tris(2,6-diphenyphenoxide) in an asymmetric 1,4-addition", Angew. Chem. Int. Ed., 2004, vol. 43, pp. 994-997.
Saito, S., et al., "Aluminum trisphenoxide polymer as a lewis acidic, solid catalyst", Synlett, 1999, No. 1, pp. 57-58.
Wang, Z. Y., et al., "Synthesis of 2,6-diphenyl-4,4'-(1-methylethylidene)bisphenol and 2,2',6,6'-tetraphenyl-4,4'-(1-methylethylidene)bisphenol", Synthesis, 1989, 471-472.
Blicke, F. F., et al., "The action of aluminum chloride on the diphenyl ester of isophthalic, terephthalic and naphthalic acids", Journal of the American Chemical Society, 1938, vol. 60, No. 10, pp. 2283-2285.
Maier, G., et al., "Diastereoselektivität bei der hydridreduktion acyclischer diketone (1,2-, 1,3-, 1,4- und 1,5-induktion", Chem. Ber., 1985, vol. 118, pp. 704-721.
Závada, J., et al., "Silver perchlorate promoted reactions: Arylmethylation of aromatics by bromomethylarenes", Collection Czechoslov. Chem. Comm., 1976, vol. 41, pp. 1777-1790.
Allmand, A. J., et al., "The alcohols of the hydroaromatic and terpene series. Part III", Journal of the Chemical Society, 1920, vol. 117, pp. 819-1263.
Grassman, W., et al., "Die stereochemie der isomeren isoputegone. Darstellung von (+)-iso-isopulegon durch thermische isomerisierung von (+)-Pulegon", Chemische Berichte, 1962, vol. 95, pp. 1400-1408.
Sayari, A., et al., "Nouveaux catalyseurs aérogels à base d'oxyde de nickel pour la transformation des alcénes en nitriles au moyen d'oxyde d'azote. III. Activité et sélectivité catalytiques de la phase spinelle Ni Al$_2$O$_4$", Bulletin de la Société Chimique de France, 1981, pp. I-24-I-27.
Otsuka, S., et al., "Catalytic asymmetric hydrogen migration of allylamines" Synthesis, 1991, pp. 665-680.

*Primary Examiner*—Sikarl A Witherspoon
(74) *Attorney, Agent, or Firm*—Connolly Bove Lodge & Hutz LLP

(57) ABSTRACT

The present invention relates to diarylphenoxyaluminum compounds which are obtainable by reacting a bis(diarylphenol) ligand of the formula (I)

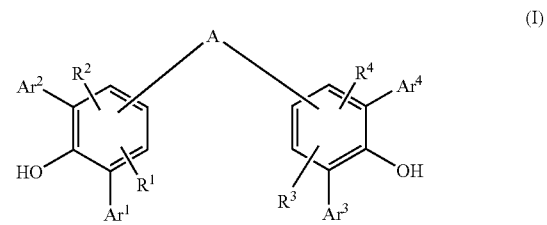

with an alkylaluminum compound and/or a complex aluminum hydride.

The invention moreover relates to the use of such diarylphenoxyaluminum compounds as catalysts.

Moreover, the invention relates to a method of producing isopulegol by cyclization of citronellal in the presence of diarylphenoxyaluminum compounds as catalysts.

The invention also relates to a method of producing menthol by cyclization of citronellal in the presence of diarylphenoxyaluminum compounds as catalysts and subsequent hydrogenation.

25 Claims, No Drawings

DIARYLPHENOXY ALUMINUM COMPOUNDS

RELATED APPLICATIONS

This application is a national stage application (under 35 U.S.C. 371) of PCT/EP2006/060416 filed Mar. 3, 2006, which claims benefit of German application 10 2005 010 329.4 filed Mar. 3, 2005, and German application 10 2005 044 518.7 filed Sep. 16, 2005.

TECHNICAL FIELD OF THE INVENTION

The present invention relates to diarylphenoxyaluminum compounds which are obtainable by reacting a bis(diarylphenol) ligand of the formula (I)

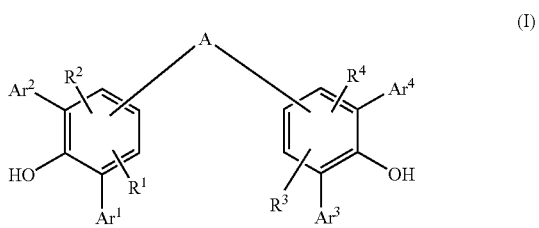

with an alkylaluminum compound and/or a complex aluminum hydride.

The invention moreover relates to the use of such diarylphenoxyaluminum compounds as catalysts.

Moreover, the invention relates to a method of producing isopulegol and diastereomer mixtures of isopulegol by cyclization of citronellal in the presence of diarylphenoxyaluminum compounds as catalysts.

In terms of amount, menthol is the most important aroma chemical worldwide. The demand for menthol continues to be covered largely by isolation from natural sources. In addition, however, there are also synthetic routes to menthol, sometimes in racemic form, sometimes in the form of the natural enantiomer L-menthol.

An important intermediate for the production of racemic and optically active menthol is isopulegol, which is usually produced by cyclizing oxo-ene reaction of citronella in the presence of Lewis-acidic catalysts and is usually produced in the form of mixtures of the four diastereomers isopulegol, iso-isopulegol, neo-isopulegol and neoiso-isopulegol.

PRIOR ART

Suitable catalysts which have been described for carrying out the abovementioned cyclization of citronella to isopulegol are both heterogeneous catalysts, such as SiO2, Al$_2$O$_3$/SiO$_2$, SiO$_2$/ZrO$_2$, SiO$_2$/TiO$_2$ mixed catalysts, mordenites, fajausites, montmorillonites and zeolites—and also homogeneous catalysts, such as, for example, sulfonic acids or Lewis acids, such as, for example, SnCl$_4$, ZnCl$_2$ or ZnBr$_2$.

An industrially used catalyst for the cyclization of citronellal is zinc bromide. However, using this catalyst, only yields of about 87% and diastereoselectivities of 91:9 (ratio of isopulegol to the other isomers of isopulegol) are obtained.

EP-A 1 225 163 describes the cyclization of citronellal to isopulegol in the presence of tris(2,6-diphenylphenol)aluminum catalysts. Tris(2,6-diphenylphenol)aluminum is known in the literature and described as catalyst for selective 1,4-functionalizations of α,β-unsaturated carbonyl compounds and for specific Claisen rearrangements, for example in Angew. Chem. Int. Ed. 2004, 43, 994.

S. Saito et al. describe, in Synlett, 1, 57-58, an aluminum trisphenoxide polymer and its use as Lewis-acidic catalyst for carrying out Diels-Aider reactions of α,β-unsaturated aldehydes as dienophiles with dienes. The specified trisphenoxide polymer is obtained by reacting 4,4'-(2,6,2',6'-tetraphenyl)biphenol with trimethylaluminum in toluene with ultrasound treatment. By-products of the desired Diels-Alder adducts described are dimeric esters as a result of a downstream Tishchenko reaction.

JP 9-278817 A relates to catalysts for olefin polymerization which are suitable as replacement for aluminoxanes. The catalysts comprise (a) a transition metal of groups 4 to 6 of the Periodic Table of the Elements which is bonded to a cyclopentadienyl system or two bridged cyclopentadienyl systems, (b) an aluminumalkyl and (c) an aromatic compound with at least two hydroxy groups bonded to the aromatic ring.

OBJECT OF THE INVENTION

In the method, regarded as being the closest prior art, for the cyclization of citronellal to isopulegol in the presence of tris(2,6-diphenylphenol)aluminum catalysts according to EP-A 1 225 163, the catalyst complexes used are expensive and can only be manufactured in a complex manner, A disadvantage of the described method, which is to be carried out in a homogeneous phase, is that recovery of the catalyst complexes used is not possible since the catalyst complex is hydrolyzed after the reaction is complete. Also, possible recovery and reusability of the ligand released in the process is not described.

Accordingly, it was an object of the present invention to provide a catalyst system which catalyzes the cyclization of citronellal to isopulegol at least as well as known catalyst systems and which either, when the reaction is complete, can be recovered in a technically simple manner and also in high purity and yield and reused, or its ligands can, after the reaction has taken place, be recovered in a technically simple way and also in high purity and yield and reused.

DESCRIPTION OF THE INVENTION AND THE PREFERRED EMBODIMENTS

The object was achieved according to the invention through the provision of diarylphenoxyaluminum compounds which are obtainable by reacting a bis(diarylphenol) ligand of the formula (I)

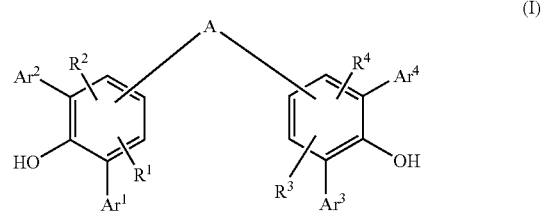

where
Ar$^1$, Ar$^2$, Ar$^3$, Ar$^4$ are identical or different and in each case, independently of one another, are an aryl radical having 6 to 15 carbon atoms or a heteroaryl radical having 2 to 15 carbon atoms which, if appropriate, can in each case carry 1 to 7 identical or different substituents selected from the group of substituents C$_1$- to C$_6$-alkyl, C$_1$- to C$_6$-perfluoroalkyl, $C_1$- to $C_6$-alkoxy, $C_7$- to $C_{12}$-aralkyl, halogen, $-SiR^{5a}R^{6a}R^{7a}$, substituted or unsubstituted $C_6$- to $C_{10}$-aryl, $-NR^{8a}R^{9a}$, $-SR^{10a}$ and $-NO_2$, $R^1$, $R^2$, $R^3$, $R^4$ are identical or different and in each case, independently of one another, are hydrogen, $C_1$- to $C_6$-alkyl, $C_1$- to $C_6$-perfluoroalkyl, $C_1$- to $C_6$-alkoxy, $C_7$- to $C_{12}$-aralkyl, halogen, $-SiR^{5b}R^{6b}R^{7b}$, substituted or unsubstituted $C_6$- to $C_{10}$-aryl, $-NR^{8b}R^{9b}$, $-SR^{10b}$ and/or $-NO_2$, and $R^1$ or $R^2$ and/or $R^3$ or $R^4$, together with A, can form an aromatic or nonaromatic cycle, and A (1) is a straight-chain or branched and/or cyclic hydrocarbon radical having 1 to 25 carbon atoms which may be saturated or mono- or polyunsaturated and/or partially aromatic and, if appropriate, can have one or more identical or different hetero atoms selected from the group of hetero atoms O, S and $NR^{11}$, and/or one or more identical or different functional groups selected from the group of functional groups C(O), S(O) and S(O)$_2$, and, if appropriate, can carry one or more identical or different substituents selected from the group of substituents $C_1$- to $C_6$-alkyl, $C_1$- to $C_6$-perfluoroalkyl, $C_1$- to $C_6$-alkoxy, $C_1$- to $C_{10}$-acyloxy, $C_7$- to $C_{12}$-aralkyl, halogen, $-SiR^{5c}R^{6c}R^{7c}$, substituted or unsubstituted $C_6$- to $C_{10}$-aryl, substituted or unsubstituted $C_2$- to $C_{10}$-hetaryl, $-NR^{6c}R^{9c}$, $-SR^{10c}$, $-NO_2$, $C_1$- to $C_{12}$-acyl and $C_1$- to $C_{10}$-carboxyl, or (2) is an aryl radical having 6 to 15 carbon atoms or a heteroaryl radical having 2 to 15 carbon atoms which, if appropriate, can in each case carry 1 to 5 substituents, selected from the group of substituents $C_1$- to $C_6$-alkyl, $C_1$- to $C_6$-perfluoroalkyl, $C_1$- to $C_6$-alkoxy, $C_7$- to $C_{12}$-aralkyl, halogen, $-SiR^{5d}R^{6d}R^{7d}$, substituted or unsubstituted $C_6$- to $C_{10}$-aryl, $-NR^{8d}R^{9d}$, $SR^{10d}$ and $NO_2$, or (3) is a functional group or a hetero atom selected from the group $-O-$, $-S-$, $-N(R^{11})-$, $-S(O)-$, $-C(O)-$, $-S(O)_2-$, $-P(R^{11})-$, $-(R^{11})P(O)-$ and $-Si(R^{12}R^{13})$, where the radicals $R^{5a}$, $R^{6a}$, $R^{7a}$, $R^{8a}$, $R^{9a}$, $R^{10a}$ to $R^{5d, R6d}$, $R^{7d}$, $R^{8d}$, $R^{9d}$, $R^{10d}$ and $R^{11}$ to $R^{13}$ are in each case, independently of one another, $C_1$- to $C_6$-alkyl, $C_7$- to $C_{12}$-aralkyl and/or substituted or unsubstituted $C_6$- to $C_{10}$-aryl, and the radicals $R^{8a}$ and $R^{9a}$, $R^{8b}$ and $R^{9b}$, $R^{8c}$ and $R^{9c}$, $R^{8d}$ and $R^{9d}$, independently of one another, can in each case together also form a cyclic hydrocarbon radical having 2 to 8 carbon atoms which can have one or more identical or different hetero atoms selected from the group O, S and $NR^{11a}$ and $R^{11a}$ can have the meanings given for $R^{11}$, with an aluminum compound of the formula (II)

$$(R^{14})_{3-p}AlH_p \qquad (II),$$

where
Al is aluminum and
$R^{14}$ is a branched or unbranched alkyl radical having 1 to 5 carbon atoms and
p is 0 or an integer from 1 to 3,
and/or
with an aluminum compound of the formula (III)

$$MAlH_4 \qquad (III),$$

where
Al is aluminum and
M is lithium, sodium or potassium.

The bis(diarylphenol) ligands of the formula (I) to be used for producing the diarylphenoxyaluminum compounds according to the invention have two phenol systems which are in each case substituted in both ortho positions relative to the phenolic hydroxy group by aromatics or heteroaromatics ($Ar^1$ to $Ar^4$) and are joined together via a structural element A and can, if appropriate, also carry further substituents ($R^1$ to $R^4$).

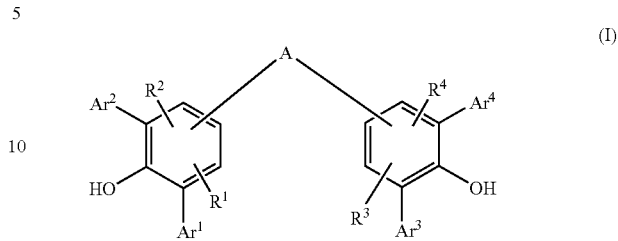

(I)

The aromatic or heteroaromatic substituents $Ar^1$ to $Ar^4$ can, independently of one another, be identical or different. Preferably, the two substituents bonded in each case to a phenol system ($Ar^1$ and $Ar^2$ or $Ar^3$ and $Ar^4$) are pairwise identical. Particularly preferably, all four substituents $Ar^1$ to $Ar^4$ are identical, The specified substituents $Ar^1$ to $Ar^4$ are aryl radicals having 6 to 15, preferably 6 to 10, carbon atoms or heteroaryl radicals having 2 to 15, preferably 3 to 10, carbon atoms in the aromatic ring system.

Examples of aryl radicals having 6 to 15 carbon atoms which may be mentioned are: phenyl, naphthyl, anthracenyl, preferably phenyl and naphthyl.

The specified heteroaryl radicals having 2 to 15 carbon atoms have 1 to about 6, generally 1 to 3, identical or different hetero atoms which are selected from the group of hetero atoms O, S and N. Examples thereof which may be mentioned are the following heteroaryl radicals: 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, benzofuryl, isobenzofuryl, benzothienyl, indolyl, isoindolyl, carbazolyl, pyridyl, quinolyl, isoquinolyl and pyrazyl. Preferred heteroaryl radicals are, for example: 2-furyl, 2-pyridyl, 2-imidazoyl.

The aryl or heteroaryl radicals specified above for $Ar^1$ to $Ar^4$ can in each case, independently of one another, be unsubstituted or carry 1 to about 7, preferably 1 to 3, in particular 1 or 2, identical or different substituents which are selected from the group of substituents: $C_1$- to $C_6$-alkyl, $C_1$- to $C_6$-perfluoroalkyl, $C_1$- to $C_6$-alkoxy, $C_7$- to $C_{12}$-aralkyl, halogen, $-SiR^{5a}R^{6a}R^{7a}$, substituted or unsubstituted $C_6$- to $C_{10}$-aryl, $-NR^{8a}R^{9a}$, $-SR^{10a}$, $-NO_2$, where the radicals $R^{5a}$, $R^{6a}$, $R^{7a}$, $R^{8a}$, $R^{9a}$, $R^{10a}$ and $R^{11}$ to $R^{13}$ are in each case, independently of one another, $C_1$- to $C_6$-alkyl, $C_7$- to $C_{12}$-aralkyl and/or substituted or unsubstituted $C_6$- to $C_{10}$-aryl, and the radicals $R^{8a}$ and $R^{9a}$, independently of one another, can in each case together also form a cyclic hydrocarbon radical having 2 to 3 carbon atoms which can have one or more identical or different hetero atoms selected from the group O, S and $NR^{11a}$, and $R^{11a}$ can have the meanings given for $R^{11}$.

In this connection, the specified substituents within the scope of the overall present invention can be attributed the meanings given by way of example below:

$C_1$-$C_6$-Alkyl, such as, for example, methyl, ethyl, propyl, 1-methylethyl, butyl, 1-methylpropyl, 2-methylpropyl, 1,1-dimethylethyl, pentyl, cyclopentyl, 1-methylbutyl, 2-methylbutyl, 3-methylbutyl, 2,2-dimethylpropyl, 1-ethylpropyl, hexyl, cyclohexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$- to $C_6$-Perfluoroalkyl, such as, for example, trifluoromethyl, pentafluoroethyl, heptafluoropropyl, heptafluoroisopropyl, nonafluorobutyl;

$C_1$- to $C_6$-Alkoxy, such as, for example, methoxy, ethoxy, propoxy, 1-methylethoxy, butoxy, 1-methylpropoxy, 2-methylpropoxy and 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_7$- to $C_{12}$-Aralkyl, such as, for example, benzyl, 1-phenylethyl, 2-phenylethyl;

$C_1$- to $C_{10}$-Acyloxy, such as, for example, acetyloxy, propionyloxy;

$C_1$- to $C_{10}$-Carboxyl, such as, for example, methoxycarbonyl, ethoxycarbonyl, propyloxycarbonyl, isopropyloxycarbonyl;

$C_1$- to $C_{10}$-Acyl, such as, for example, formyl, acetyl, propionyl.

The term substituted or unsubstituted $C_6$- to $C_{10}$-aryl is to be understood as meaning aryl radicals as specified above which have one or more, generally 1 to about 3, identical or different substituents, where the substituents can be selected, for example, from the substituents, as specified above and below, $C_1$- to $C_6$-alkyl, $C_1$- to $C_{-6}$-perfluoroalkyl, $C_1$- to $C_6$-alkoxy, $C_7$- to $C_{12}$-aralkyl, halogen, silyl, dialkylamino and nitro.

Within the scope of the present invention, the term halogen is to be understood as meaning fluorine, chlorine, bromine and iodine, preferably fluorine and chlorine.

Within the scope of the present invention, the substituents —$SiR^{5a}R^{6a}R^{7a}$ to —$SiR^{5d}R^{6d}R^{7d}$ are in each case silyl substituents each having, independently of one another, three identical or different radicals which are selected from the radicals $C_1$- to $C_6$-alkyl, $C_7$- to $C_{12}$-aralkyl and substituted or unsubstituted $C_6$- to $C_{10}$-aryl. By way of example, mention may be made here of, say, the silyl substituents trimethylsilyl, triethylsilyl, tert-butyldimethylsilyl and tert-butyldiphenylsilyl.

Within the scope of the present invention, the substituents —$NR^{8a}R^{9a}$ to —$NR^{8d}R^{9d}$ are in each case amino substituents which each, independently of one another, carry two identical or different, preferably two identical, radicals which are selected from the above-described radicals $C_1$- to $C_6$-alkyl, $C_7$- to $C_{12}$-aralkyl and/or substituted or unsubstituted $C_6$- to $C_{10}$-aryl. By way of example, amino substituents which may be mentioned are: dimethylamino, diethylamino, dibenzylamino, diallylamino, diisopropylamino. Within the scope of the present invention, the radicals $R^{8a}$ and $R^{9a}$ to $R^{8d}$ and $R^{9d}$ can, independently of one another, in each case together also form a cyclic hydrocarbon radical having 2 to 8 carbon atoms which can have one or more identical or different hetero atoms selected from the group O, S, $NR^{11a}$. The radical $R^{11a}$ can here be an above-described $C_1$- to $C_6$-alkyl, $C_7$- to $C_{12}$-aralkyl and/or substituted or unsubstituted $C_6$- to $C_{10}$-aryl. Examples of these cyclic substituents $R^{8a}$ and $R^{9a}$ to $R^{8d}$ and $R^{9d}$ which may be mentioned are: piperidinyl, morpholinyl, N-methylpiperazinyl, N-benzyl-piperazinyl.

In the substituents —$SR^{10a}$, the radical $R^{10a}$ is an above-defined $C_1$- to $C_6$-alkyl, $C_7$- to $C_{12}$-aralkyl and/or substituted or unsubstituted $C6$- to $C_{10}$-aryl, preferably methyl, ethyl, isopropyl, phenyl, benzyl.

Examples of aromatic or heteroaromatic substituents $Ar^1$, $Ar^2$, $Ar^3$, $Ar^4$ preferred within the scope of the present invention that may be mentioned are: phenyl, 4-methylphenyl, 2,4,6-trimethylphenyl, naphthyl, 2-fluorophenyl, 4-fluorophenyl, 4-chlorophenyl, 4-bromophenyl, 3-fluorophenyl, 3-chlorophenyl, 3,5-difluorophenyl, 3,5-dichlorophenyl, 2,3,6-trichlorophenyl, 2,4,6-trichlorophenyl, 2-methylphenyl, 4-methylphenyl, 2,4,5-trimethylphenyl, 2,4,6-trirmethylphenyl, 2-isopropylphenyl, 4-isopropylphenyl, 4-tert-butylphenyl, 4-n-butylphenyl, 3-trifluoromethylphenyl, 4-trifluoromethylphenyl, 3,5-bis(trifluoromethyl)phenyl, 4-arylphenyl, 3-nitrophenyl, preferably 4-fluorophenyl, 4-chlorophenyl, 3-chlorophenyl, 3,5-dichlorophenyl, 3-trifluoromethylphenyl, 4-trifluoromethylphenyl. Within the scope of a preferred embodiment, the radicals $Ar^1$, $Ar^2$, $Ar^3$, $Ar^4$ are identical and are preferably 4-fluorophenyl, 4-chlorophenyl, 3-chlorophenyl, 3,5-dichlorophenyl, 3trifluoromethylphenyl, 4-trifluoromethylphenyl, particularly preferably phenyl.

According to the invention, the substituents $R^1$, $R^2$, $R^3$, $R^4$ in the meta or para position relative to the respective phenolic hydroxy groups may be identical or different, preferably identical and are in each case, independently of one another, hydrogen and/or an abovementioned $C_1$- to $C_6$-alkyl, $C_1$- to $C_6$-perfluoroalkyl, $C_1$- to $C_6$-alkoxy, $C_7$- to $C_{12}$-aralkyl, halogen, —$SiR^{5b}R^{6b}$, $R^{7b}$, substituted or unsubstituted $C_6$- to $C_{10}$-aryl, —$NR^{8b}R^{9b}$, —$SR^{10b}$ and/or —$NO_2$.

Preferred radicals $R^1$, $R^2$, $R^3$, $R^4$ which may be mentioned are: methyl, ethyl, isopropyl, halogen, in particular fluorine and/or chlorine, trifluoromethyl, phenyl, methoxy, nitro. Preferably, the radicals $R^1$, $R^2$, $R^3$, $R^4$ are identical and are particularly preferably hydrogen.

The radicals $R^1$ or $R^2$ and/or $R^3$ or $R^4$ can, together with the structural element A, also form a cyclic aromatic or nonaromatic cycle. In these cases, the bis(diarylphenol) ligands of the formula (I) to be used according to the present invention have a tricyclic basic structure, for example an anthracene basic structure of the formula (X) or basic structures of the type (XI):

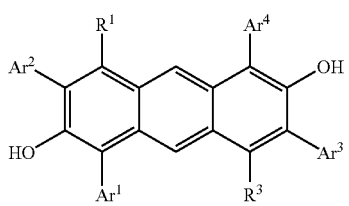

(X)

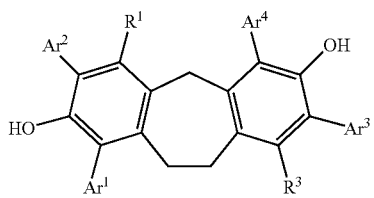

(XI)

Further structural modifications of these tricyclic basic structures, if appropriate including those which have hetero atoms in the basic structure, are known to the person skilled in the art and belong to the group of bis(diarylphenol) ligands which can be used according to the invention.

The structural element A in formula (I) can be a straight-chain or branched and/or cyclic hydrocarbon radical having 1 to 25 carbon atoms, which may be saturated or mono- or polyunsaturated, normally 1 to about 6-fold unsaturated and/or may be partially aromatic. The specified hydrocarbon radicals can, if appropriate, have one or more, generally 1 to 3, identical or different hetero atoms selected from the group of hetero atoms O, S and $NR^{11}$ and/or one or more identical or different functional groups selected from the group of functional groups C(O), S(O) and $S(O)_2$, and if appropriate carry one or more identical or different substituents selected from the group of substituents $C_1$- to $C_6$-alkyl, $C_1$- to $C_6$-perfluoroalkyl, $C_1$- to $C_6$-alkoxy, $C_1$- to $C_{10}$-acyloxy, $C_7$- to $C_{12}$-aralkyl, halogen, $-SiR^{5c}R^{6c}R^{7c}$, substituted or unsubstituted $C_6$- to $C_{10}$-aryl, substituted or unsubstituted $C_2$- to $C_{10}$-hetaryl, $-NR^{8c}R^{9c}$, $-SR^{10c}$, $-NO_2$, $C_1$- to $C_{12}$-acyl and $C_1$- to $C_{10}$-carboxyl.

Preferably, the structural element A in formula (I) is a straight-chain or branched and/or cyclic hydrocarbon radical having 1 to 25, preferably 1 to 15, and particularly preferably 1 to 10, carbon atoms which may be saturated or mono- to triunsaturated and/or may be partially aromatic. The preferred hydrocarbon radicals can, if appropriate, have one or more, generally 1 to 3, identical or different hetero atoms selected from the group of hetero atoms O, S and $NR^{11}$ and/or one or more C(O) groups and, if appropriate, carry one or more identical or different substituents selected from the group of substituents $C_1$- to $C_6$-alkyl, $C_1$- to $C_6$-perfluoroalkyl, $C_1$- to $C_6$-alkoxy, $C_1$- to $C_{10}$-acyloxy, $C_7$- to $C_{12}$-aralkyl, halogen, substituted or unsubstituted $C_6$- to $C_{10}$-aryl, $-NO_2$, $C_1$- to $C_{12}$-acyl and $C_1$- to $C_{10}$-carboxyl.

Examples of structural elements A in the formula (I) which may be mentioned without any limiting character are the following structural elements 1 to 44, where the wavy lines in each case mark, as within the scope of the entire present disclosure, the linkage sites to the remainder of the respective ligand structure:

1
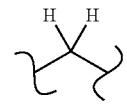

2
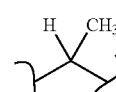

3
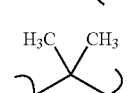

4
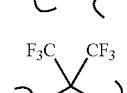

5
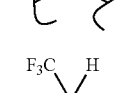

6
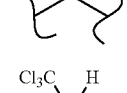

7
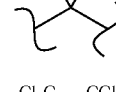

8

9
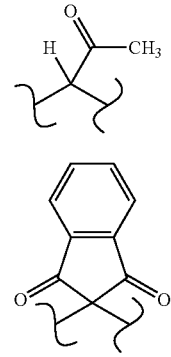

10
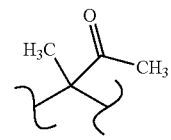

11
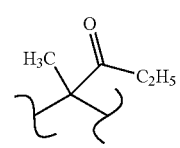

12
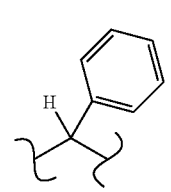

-continued
| | |
|---|---|
| 13 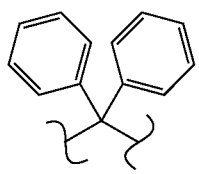 | 21 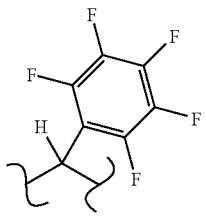 |
| 14 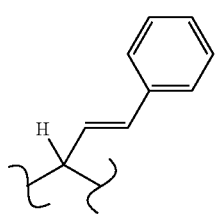 | 22 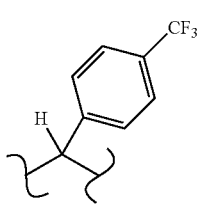 |
| 15 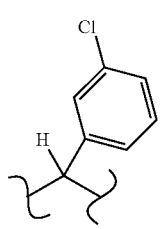 | 23 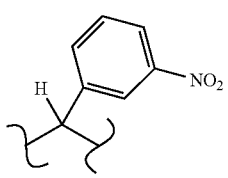 |
| 16 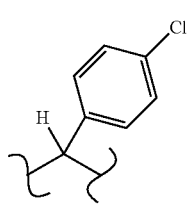 | 24 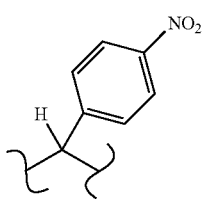 |
| 17 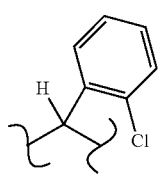 | 25 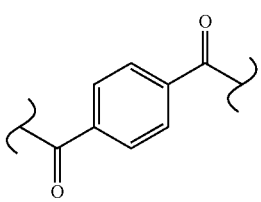 |
| 18 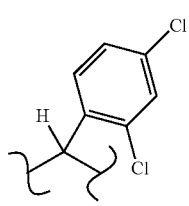 | 26 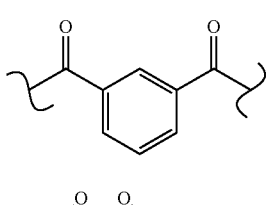 |
| 19 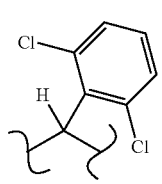 | 27 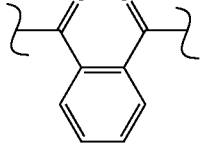 |
| 20 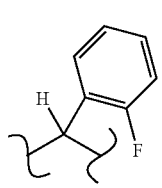 | 28 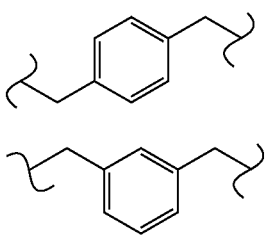 |
| | 29 |

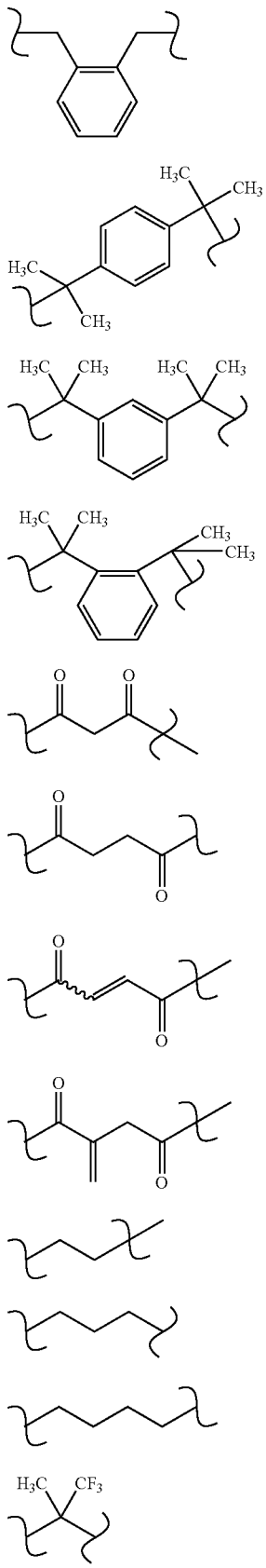

The structural elements 1 to 44 shown can also in each case carry the substituents as referred to above and, if appropriate, have further, normally 1 or 2, ethylenic double bonds.

The structural element A can also be an aryl radical having 6 to 15, preferably 6 to 10, carbon atoms, specifically a phenylene, naphthylene or anthracenylene radical, or a heteroaryl radical as defined above having 2 to 15, preferably 3 to 10, carbon atoms.

The specified aryl and heteroaryl radicals can, if appropriate, in each case carry 1 to 5 substituents which are selected from the group of the above-described substituents $C_1$- to $C_6$-alkyl, $C_1$- to $C_6$-perfluoroalkyl, $C_1$- to $C_6$-alkoxy, $C_7$- to $C_{12}$-aralkyl, halogen, —$SiR^{5d}R^{6d}$, $R^{7d}$, substituted or unsubstituted $C_6$- to $C_{10}$-aryl, —$NR^{8d}R^{9d}$, $SR^{10d}$ and $NO_2$.

Furthermore, the structural element A can also be a functional group or a hetero atom which are selected from the group —O—, —S—, —N($R^{11}$)—, —S(O)—, —C(O)—, —S(O)$_2$—, —P($R^{11}$)—, —($R^{11}$)P(O)—, —OP(O)O—, —OP(O)$_2$O— and —Si($R^{12}$)($R^{13}$)—, where the radicals $R^{11}$, $R^{12}$, $R^{13}$, independently of one another, are in each case an above-described $C_1$- to $C_6$-alkyl, $C_7$- to $C_{12}$-aralkyl and/or substituted or unsubstituted $C_6$- to $C_{10}$-aryl. Within the scope of this group, the structural element A is preferably —O—, —S—, —S(O)—, S(O)$_2$— or —Si($R^{12}$)($R^{13}$)—.

Diarylphenoxyaluminum compounds preferred within the scope of the present invention are those which are obtainable by reacting bis(diarylphenol) ligands of the formula (Ia)

$$\text{(Ia)}$$

with an aluminum compound of the formula (II) and/or (III).

The ligands of the formula (Ia) likewise have two phenol systems which are in each case substituted in the two ortho positions relative to the phenolic hydroxy group by aromatics or heteroaromatics ($Ar^1$ to $Ar^4$) and are joined together via a structural element A and, if appropriate, can also carry further substituents ($R^1$ to $R^4$), where the structural element A is joined to the two phenol systems in each case in the para position relative to the phenolic hydroxy group. Here, the radicals $Ar^1$, $Ar^2$, $Ar^3$, $Ar^4$, the radicals $R^1$, $R^2$, $R^3$, $R^4$ and the structural element A can be attributed the same meanings as specified above for formula (I).

According to the invention, particularly preferred ligands are those in which the aryl radicals $Ar^1$, $Ar^2$, $Ar^3$ and $Ar^4$ are identical and have the preferred meanings stated above for formula (I). Particularly preferred aryl radicals $Ar^1$ to $Ar^4$ are phenyl, naphthyl, 4-fluorophenyl, 4-chlorophenyl, 3-chlorophenyl, 3,5-dichlorophenyl, 4-methylphenyl, 3-trifluoromethylphenyl, 4trifluoromethylphenyl, very particularly preferably phenyl.

In the ligands of the formula (Ia) preferred according to the invention, the radicals $R^1$, $R^2$, $R^3$, $R^4$ are identical or different, preferably identical, and are preferably: hydrogen, halogen, in particular fluorine or chlorine, methyl, trifluoromethyl, isopropyl, tert-butyl, phenyl, nitro.

The structural element A in formula (Ia) is attributed the meanings specified above for formula (I). Preferred structural elements A in formula (Ia) are, in particular, also the structural elements 1 to 44 which can be substituted in the specified manner.

Particularly preferred ligands are those of the formulae ($Ia_1$) to ($Ia_3$), where the specified radicals $Ar^1$ to $Ar^4$, $R^1$ to $R^4$ and $R^{15}$ to $R^{18}$ are preferably attributed the meanings listed in the table by way of example:

TABLE 1

($Ia_1$)

| Compound | $Ar^1$ | $Ar^2$ | $Ar^3$ | $Ar^4$ | $R^1$ | $R^2$ | $R^3$ | $R^4$ | $R^{15}$ |
|---|---|---|---|---|---|---|---|---|---|
| $Ia_1$-1 | Ph | Ph | Ph | Ph | H | H | H | H | H |
| $Ia_1$-2 | Ph | Ph | Ph | Ph | H | H | H | H | $CH_3$ |
| $Ia_1$-3 | Ph | Ph | Ph | Ph | H | H | H | H | Ph |
| $Ia_1$-4 | Ph | Ph | Ph | Ph | H | H | H | H | $CF_3$ |
| $Ia_1$-5 | Ph | Ph | Ph | Ph | H | H | H | H | $CCl_3$ |
| $Ia_1$-6 | Ph | Ph | Ph | Ph | H | H | H | H | 4-Cl-Ph |
| $Ia_1$-7 | Ph | Ph | Ph | Ph | H | H | H | H | $CH_2CH_3$ |
| $Ia_1$-8 | Ph | Ph | Ph | Ph | H | H | H | H | 3-$NO_2$-Ph |
| $Ia_1$-9 | Ph | Ph | Ph | Ph | H | H | H | H | C(O)CH_3 |

TABLE 2

($Ia_2$)

| Compound | $Ar^1$ | $Ar^2$ | $Ar^3$ | $Ar^4$ | $R^1$ | $R^2$ | $R^3$ | $R^4$ | $R^{16}$ | $R^{17}$ |
|---|---|---|---|---|---|---|---|---|---|---|
| $Ia_2$-1 | Ph | Ph | Ph | Ph | H | H | H | H | $CF_3$ | $CF_3$ |
| $Ia_2$-2 | Ph | Ph | Ph | Ph | H | H | H | H | $CCl_3$ | $CCl_3$ |
| $Ia_2$-3 | Ph | Ph | Ph | Ph | H | H | H | H | $CH_3$ | $CF_3$ |
| $Ia_2$-4 | Ph | Ph | Ph | Ph | H | H | H | H | $CH_3$ | $CCl_3$ |
| $Ia_2$-5 | Ph | Ph | Ph | Ph | H | H | H | H | $CH_2CH_3$ | $CF_3$ |
| $Ia_2$-6 | Ph | Ph | Ph | Ph | H | H | H | H | $CH_3$ | $CH_3$ |
| $Ia_2$-7 | Ph | Ph | Ph | Ph | H | H | H | H | $CH_3$ | $C(O)OCH_3$ |
| $Ia_2$-8 | Ph | Ph | Ph | Ph | H | H | H | H | $CH_3$ | $C(O)OC_2H_5$ |
| $Ia_2$-9 | Ph | Ph | Ph | Ph | H | H | H | H | —$(CH_2)_3$— | |
| $Ia_2$-10 | Ph | Ph | Ph | Ph | H | H | H | H | —$(CH_2)_4$— | |
| $Ia_2$-11 | Ph | Ph | Ph | Ph | H | H | H | H | —$(CH_2)_5$— | |

TABLE 3
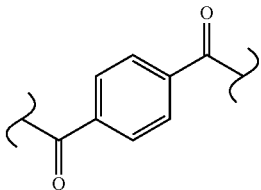
(Ia₃)
| Compound | Ar¹ | Ar² | Ar³ | Ar⁴ | R¹ | R² | R³ | R⁴ | R¹⁸ |
|---|---|---|---|---|---|---|---|---|---|
| Ia₃-1 | Ph | Ph | Ph | Ph | H | H | H | H | —(CH₂)₂— |
| Ia₃-2 | Ph | Ph | Ph | Ph | H | H | H | H | 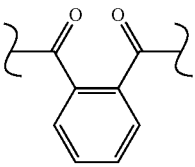 |
| Ia₃-3 | Ph | Ph | Ph | Ph | H | H | H | H | 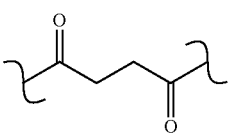 |
| Ia₃-4 | Ph | Ph | Ph | Ph | H | H | H | H | 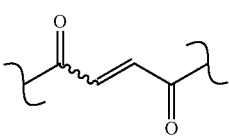 |
| Ia₃-5 | Ph | Ph | Ph | Ph | H | H | H | H | 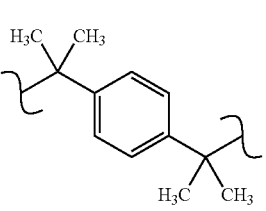 |
| Ia₃-6 | Ph | Ph | Ph | Ph | H | H | H | H | 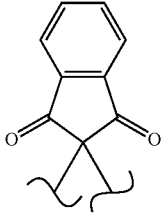 |
| Ia₃-7 | Ph | Ph | Ph | Ph | H | H | H | H |  |

Here, in tables 1-3, Ph is a phenyl radical and C(O) is, as in the scope of the entire present invention, a carbonyl group. In general, the radicals $R^{15}$, $R^{16}$ and $R^{17}$, independently of one another, can be an above-defined $C_1$- to $C_8$-alkyl, $C_1$- to $C_{10}$-acyl, $C_1$- to $C_{10}$-carboxyl or $C_6$- to $C_{10}$-aryl, where the specified radicals can carry one or more identical or different halogen and/or $NO_2$ substituents and where the radicals $R^{16}$ and $R^{17}$ can together also form a cyclic structural element, preferably an alkylene bridge.

The bis(diarylphenol) ligands of the formulae (I) or (Ia) which can be used for producing the diarylphenoxyaluminum compounds according to the invention can be prepared easily by methods known per se to the person skilled in the art. Compounds of structure type ($Ia_1$) are obtainable, for example, by reacting the corresponding bis-ortho-arylphenols with an aldehyde $R^{15}CHO$ in the presence of a Lewis acid, for example $AlCl_3$, as described, inter alia, by Z. Y. Wang, A. S. Hay in Synthesis 1989, 471-472 or in U.S. Pat. No. 3,739,035. Ligands of structure type ($Ia_2$) are, for example, accessible by reacting the corresponding bis-ortho-arylphenols with a suitable ketone of the formula $R^{18}C(O)R^{17}$, as described, for example, in U.S. Pat. No. 3,739,035. Ligands of structure type ($Ia_3$) are accessible, for example, by Friedel-Crafts acylation of the corresponding phenols or O-protected phenols with dicarboxylic acid chlorides, as described, for example, by F. F. Blicke et al. in J. Am. Chem. Soc. 1938, 60, 2283-2285; CH 350461 or by G. Maier et al. in Chem. Ber. 1985, 118, 704-721. Another way of producing ligands of structure type ($Ia_3$) also consists in the Friedel-Crafts alkylation of the corresponding phenols with tertiary diols, as described, for example, in DE-A 25 34 558, or with dihalides, as described, for example, by J. Zavada, in Collect. Czech. Chem. Commun, 1976, 41, 1777-1790.

The diarylphenoxyaluminum compounds according to the invention are obtained, for example, by reacting the above-described bis(diarylphenol) ligands of the formulae (I) or (Ia) with an aluminum compound of the formula (II)

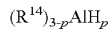  (II).

Here, $R^{14}$ is a branched or unbranched alkyl radical having 1 to 5 carbon atoms, such as, for example, methyl, ethyl, propyl, isopropyl, butyl, isobutyl, pentyl, isopentyl or neopentyl. The index p is 0 or an integer from 1 to 3. Preferably, the index p is 1 or 0, particularly preferably 0. Preferred compounds of the formula (II) are, for example, trimethylaluminum, triethylaluminum, diisobutylaluminum hydride, particularly preferably trimethylaluminum and triethylaluminum.

Alternatively to this, the diarylphenoxyaluminum compounds according to the invention are also obtained by reacting the above-described bis(diarylphenol) ligands of the formulae (I) or (Ia) with an aluminum compound of the formula (III)

  (III), where M is lithium, sodium or potassium. Consequently, of suitability for producing the diarylphenoxyaluminum compounds according to the invention by reacting the above-described bis(diarylphenol) ligands of the formulae (I) or (Ia) are also lithium aluminum hydride, sodium aluminum hydride and potassium aluminum hydride, and mixtures thereof. Moreover, mixtures of the specified compounds of the formulae (II) and (III) are also suitable for producing diarylphenoxyaluminum compounds according to the invention by reaction with the above-described bis(diarylphenol) ligands of the formulae (I) or (Ia).

The reaction is advantageously carried out such that one of the above-described bis(diarylphenol) ligands of the formulae (I) or (Ia) is brought into contact with a compound of the formula (II) or (III). The reaction is advantageously carried out in an inert organic solvent, such as, for example, toluene, cyclohexane, dichloromethane, xylene, ethylbenzene, chlorobenzene, tetrahydrofuran, diethyl ether, methyl tert-butyl ether, ethyl acetate, pentane, hexane, dichloroethane, dimethylformamide (DMF), dimethyl sulfoxide (DMSO) and the like, where the use of predried or anhydrous solvents is to be regarded as particularly advantageous. The reaction is usually carried out at temperatures in the range from about −100° C. to about 100° C., preferably at about −50° C. to about 50° C., particularly preferably at about 30° C. to about 30° C.

During the production of the diarylphenoxyaluminum compounds according to the invention, the phenolic hydroxy groups of the bis(diarylphenol) ligands of the formulae (I) or (Ia) used react with the compound or the compounds of the formulae (II) and (III).

Theoretically, each aluminum atom can react with 1 to 3 phenolic hydroxy groups. On account of the steric properties or requirements of the bis(diarylphenol) ligands of the formulae (I) or (Ia) used, this may result in the formation of higher molecular weight structures, such as linear structures or networks Here, the molar ratio of the bis(diarylphenol) ligands of the formulae (I) or (Ia) used to the compounds of the formula (II) and/or (III) used is advantageously chosen so that the amount of unreacted compounds of the formulae (II) and/or (III) is as low as possible. Preferably, the specified ratio is chosen so that, after the bis(diarylphenol) ligands of the formulae (I) or (Ia) have been brought into contact with the compound or compounds of the formulae (II) and (III), unreacted compound of the formula (II) and/or (III) is no longer present. Taking the cost aspect into consideration, it is advisable to keep the excess of ligands of the formulae (I) or (Ia) used low. Particular preference is given to using bis(diarylphenol) ligands of the formulae (I) or (Ia) and the compounds of the formulae (II) and/or (III) in a molar ratio of from about 4:1 to about 1:1, very particularly preferably from about 3:1 to about 1.5:1 and most preferably in the molar ratio of about 1.5:1.

Within the scope of a preferred embodiment of the present invention, the production of the diarylphenoxyaluminum compounds according to the invention involves initially introducing, depending on the solubility, an about 0.001 to about 1 molar solution of the selected ligand of the formula (I) or (Ia) in a suitable organic solvent, for example toluene, at a temperature of from about 10 to about 30° C., and adding an aluminum compound of the formula (II) and/or (III), preferably in the form of a solution, for example a solution of trimethyl- or triethylaluminum in toluene.

The reaction between the ligands of the formula (I) or (Ia) used and the aluminum compounds of the formulae (II) and/or (III) usually takes place rapidly and is mostly complete after about 10 min to about 2 h, often after about 1 h, depending on the reaction conditions selected. When using lower-reactivity reactants, it may be advantageous to temporarily increase the temperature of the reaction mixture.

Depending on the reaction conditions selected, in particular with regard to the solubility of the ligands of the formula (I) or (Ia) to be reacted and of the aluminum compound of the formula (II) and/or (III) in the selected solvents, the concentrations, and the reaction temperatures, the diarylphenoxyaluminum compounds according to the invention are obtained in the form of a solid, a suspension or a solution in the solvent or solvent mixture used. The diarylphenoxyaluminum compounds according to the invention obtained in this way can be further used in the form obtained in each case or be separated off and freed from the solvents used.

Isolation can take place here by methods which appear to be advantageous and are known to the person skilled in the art. Preferably, the isolation, storage and further treatment of the diarylphenoxyaluminum compounds according to the invention are carried out with extensive exclusion of oxygen and moisture.

The diarylphenoxyaluminum compounds according to the invention are suitable to a particular degree as catalysts for carrying out chemical reactions, specifically reactions or conversions of organic compounds. Accordingly, a further aspect of the present invention relates to the use of the diarylphenoxyaluminum compounds according to the invention obtainable by reacting the bis(diarylphenol) ligands of the formulae (I) or (Ia) with the compounds of the formula (II) and/or (III) as catalysts. The diarylphenoxyaluminum compounds according to the invention are particularly suitable as catalysts for carrying out reactions which can be catalyzed by acids or Lewis acids. By way of example and without any limiting character, the following reaction types may be mentioned here: rearrangements, isomerizations, cyclizations, eliminations, dearomatizing nucleophilic functionalization of aromatic carbonyl compounds, conjugated addition onto α,β-unsaturated carbonyl compounds, Diels-Alder reactions.

The specified reactions are advantageously carried out under the dryest possible aprotic conditions and with the most extensive possible exclusion of oxygen.

After the reaction has taken place, the diarylphenoxyaluminum compounds used can be at least partially isolated from the reaction mixture using customary separation methods (e.g. by filtration, centrifugation) and then reused. Alternatively, however, the bis(diarylphenol) ligands of the formulae (I) or (Ia) can also be readily recovered from the crude or already worked-up reaction mixture, if appropriate also after separating off reaction products and/or by-products, since they generally have advantageous physical properties such as, for example, good crystallization ability.

The diarylphenoxyaluminum compounds according to the invention are suitable to a particular degree as catalysts for carrying out intramolecular reactions, in particular for carrying out cyclization reactions.

According to the invention, particular preference is given to the use of the diarylphenoxyaluminum compounds according to the invention as catalysts for the cyclization of racemic or nonracemic citronellal to racemic or nonracemic isopulegol. In this connection, preference is given according to the invention in particular to the diarylphenoxyaluminum compounds which are obtainable by reacting bis(diarylphenol) ligands of the formulae (Ia) with an aluminum compound of the formula (II) and/or (III). Very particular preference is given to the use of diarylphenoxyaluminum compounds which are obtainable by reacting bis(diarylphenol) ligands of the formulae (Ia$_1$) to (Ia$_3$) as catalysts for the cyclization of citronellal to isopulegol.

The present invention accordingly also relates to a method of producing isopulegol of the formula (IV)

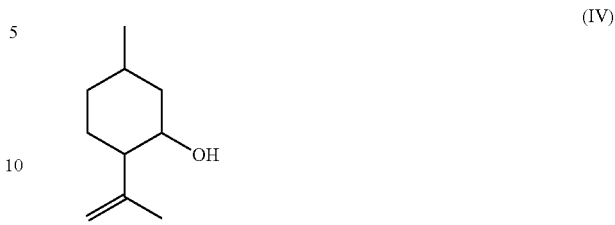

(IV)

comprising the cyclization of citronellal of the formula (V)

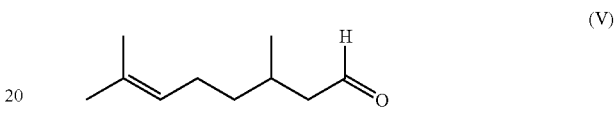

(V)

in the presence of a catalyst which is obtainable by reacting a bis(diarylphenol) ligand of the formula (I)

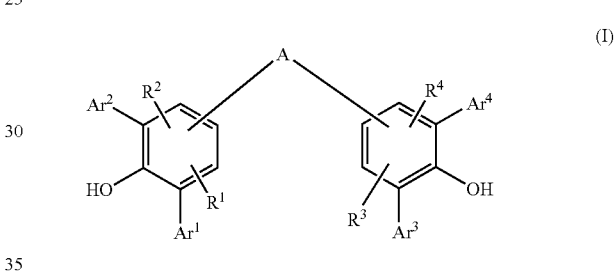

(I)

where
Ar$^1$, Ar$^2$, Ar$^3$, Ar$^4$, R$^1$, R$^2$, R$^3$, R$^4$ and A have the meanings given above for formula (I), with an aluminum compound of the formula (II)

(II), where
Al is aluminum and
R$^{14}$ is a branched or unbranched alkyl radical having 1 to 5 carbon atoms and
p is 0 or an integer from 1 to 3,
and/or
with an aluminum compound of the formula (III)

(III), where
Al is aluminum and
M is lithium, sodium or potassium.

The method is also suitable for producing optically active isopulegol of the formula (IVa)

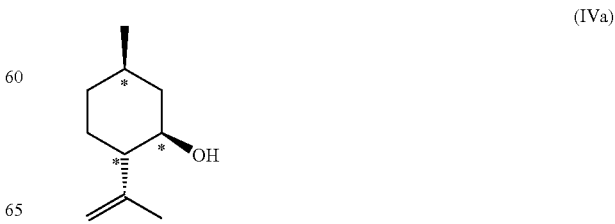

(IVa)

comprising the cyclization of optically active citronellal of the formula (Va)

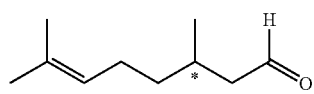

where (*) refers in each case to an asymmetric carbon atom.

The method according to the invention is particularly preferably suitable for producing L-(−)-isopulegol by cyclization of D-(+)-citronellal.

Catalysts preferred within the scope of the method according to the invention are those which are obtainable by reacting bis(diarylphenol) ligands of the formula (Ia)

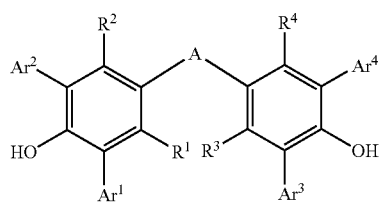

where the radicals $Ar^1$, $Ar^2$, $Ar^3$, $Ar^4$, $R^1$, $R^2$, $R^3$, $R^4$ and A have the meanings given above for formula (Ia). Among these, preference is in turn given to the above-described ligands of the formulae $(Ia_1)$ to $(Ia_3)$. Very particularly preferred ligands within the scope of the method according to the invention are the compounds $Ia_1$-1, $Ia_1$-4, $Ia_1$-5, $Ia_2$-1, and $Ia_2$-3.

The diarylphenoxyaluminum compounds according to the invention are obtained from said ligands, as described above, by reaction with an aluminum compound of the formula (II) and/or (III), preferably with an aluminum compound of the formula (II).

To carry out the method according to the invention for producing isopulegol, the procedure advantageously involves firstly providing a solution of the diarylphenoxyaluminum compounds according to the invention in a suitable solvent as described above. According to the invention, the racemic or nonracemic citronellal to be cyclized is then added to this solution. The citronellal can be added here as it is or in the form of a solution, advantageously in one of the abovementioned suitable solvents. Within the scope of a preferred embodiment of the method according to the invention, a solution of the selected ligand of the formulae (I) or (Ia) in toluene is firstly prepared and then, advantageously with stirring, the selected aluminum compound of the formula (II) and/or (III), preferably trimethylaluminum or triethylaluminum in toluenic solution is added.

A suitable starting material for carrying out the cyclization method according to the invention is citronellal, which can be produced by any method. Preference is given to using citronellal which has a purity of from about 90 to about 99.9% by weight, particularly preferably from about 95 to about 99.9% by weight.

The addition of the citronellal to be cyclized advantageously takes place at temperatures in the range from about −40° C. to about 40° C., preferably in the range from about −20° C. to about 20° C. For this purpose, the prepared solution of the diarylphenoxyaluminum compound according to the invention is advantageously cooled to a temperature in this range, e.g. to a temperature in the range from −10° C. to 10° C., and precooled citronellal or a precooled solution of citronellal is added.

The citronellal or the solution thereof can be added in such a way that either the total amount is added in one portion or it is added to the prepared catalyst solution in portions or else continuously. Suitable solvents are in turn the abovementioned solvents, in particular toluene. Preferably, the citronellal to be cyclized is used as it is, i.e. without the further addition of solvents. If a solvent is used, the total amount of solvent (for catalyst production and for carrying out the cyclization reaction) is advantageously chosen so that the volume-based ratio of citronellal to be reacted to solvent is about 2:1 to about 1:20, preferably from about 1.5:1 to about 1:10.

The quantitative ratio between the citronellal to be reacted and the amount of diarylphenoxyaluminum compound according to the invention used is determined by the amount of compounds of the formula (I) or (Ia) and of the formula (II) and/or (III) used for the production thereof, i.e. by the quantitative ratio of ligand used to aluminum compound of the formula (II) and/or (III) used.

According to the invention, the amount of citronellal to be reacted relative to the amount of aluminum compound of the formula (II) and/or (III) used is chosen such that the molar ratio is about 5:1 to about 1000:1, preferably about 10:1 to about 500:1, particularly preferably about 50:1 to about 200:1.

Irrespective of this, the ratio between ligand of the formula (I) or (Ia) used and the aluminum compound of the formula (II) and/or (III) used can be varied within the limits specified above for producing the diarylphenoxyaluminum compound according to the invention.

The cyclization according to the invention of citronellal to isopulegol generally takes place rapidly and is usually largely complete after about 0.5 to about 10 h, often after about 5 h, depending on the choice of reactants and reaction conditions. Reaction progress can be easily monitored by methods known per se to the person skilled in the art, for example by chromatographic, specifically gas-chromatographic methods, or else HPLC methods.

Using certain citronellal grades (e.g. if citronellol impurities are present in the citronellal) during the production of isopulegol by cyclization of citronellal in the presence of the above-described diarylphenoxyaluminum compounds, it has sometimes been observed that, particularly in the case of reactions on an industrial scale, an undesired secondary reaction can take place to a troublesome extent: this is the formation of citronellyl citronellate of the formula (XII)

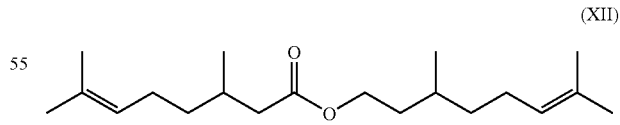

or other high-boiling impurities, which cannot be accepted among the high requirements for yield, selectivity and stability to be placed on the abovementioned reaction of a method to be carried out on an industrial scale.

Within the scope of a preferred embodiment of the method according to the invention, the cyclization of citronellal to isopulegol is carried out in the presence of an acid, preferably an organic acid. Examples of organic acids which can be used advantageously are: acetic acid, propionic acid, benzoic acid, toluenesulfonic acid, methanesulfonic acid, preferably acetic acid. The specified acids are advantageously used in an amount of from about 0.5 to about 10% by weight, based on the amount of citronellal to be reacted. They are advantageously added to the reaction mixture together with the citronellal, e.g. in the form of a mixture.

In a particularly preferred embodiment, the method according to the invention for producing isopulegol by cyclization of citronellal is carried out in the presence of at least one compound which is selected from the group of carboxylic acid anhydrides, aldehydes, ketones and vinyl ethers.

The compounds of said classes of substance can in each case be used individually or in the form of mixtures with one another. In the case of mixtures, preference is given to using those which consist of compounds from one class of substance. Particular preference is given to using individual compounds. Using the specified compounds, as described below, it is generally possible to largely suppress the formation of the undesired by-product of the formula (XII).

Within the scope of a preferred embodiment, the cyclization method according to the invention is carried out in the presence of a carboxylic acid anhydride of the formula (VI)

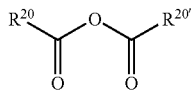

(VI)

where the radicals $R^{20}$ and $R^{21}$ can be identical or different, preferably identical, and are a branched or unbranched $C_1$- to $C_{12}$-alkyl radical or $C_7$- to $C_{12}$-aralkyl radical or a $C_6$- to $C_{10}$-aryl radical, where the specified radicals can in each case have one or more, generally 1 to about 3, identical or different substituents selected from the group $OR^{10e}$, $SR^{10f}$, $NR^{8e}R^{9e}$ and halogen and where $R^{20}$ and $R^{20'}$ can together also form a 5- to 8-membered ring which can have one or more ethylenic double bonds and one or more identical or different hetero atoms selected from the group O, S and $NR^{11b}$ and where $R^{10e}$, $R^{10f}$, $R^{8e}$, $R^{9e}$ and $R^{11b}$ can have the meanings given above for $R^{11}$.

Within the scope of a further preferred embodiment, the cyclization method according to the invention is carried out in the presence of an aldehyde of the formula (VII)

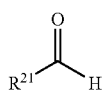

(VII)

where the radical $R^{21}$ is a branched or unbranched $C_1$- to $C_{12}$-alkyl radical or $C_7$- to $C_{12}$-aralkyl radical or a $C_6$- to $C_{10}$-aryl radical, where the specified radicals can in each case have one or more, preferably 1 to 3, identical or different substituents selected from the group $OR^{10e}$, $SR^{11f}$, $NR^{8e}R^{9e}$ and halogen, where $R^{10e}$, $R^{10f}$, $R^{8e}$ and $R^{9e}$ can have the meanings given above for $R^{11}$.

Within the scope of a further preferred embodiment, the cyclization method according to the invention is carried out in the presence of a ketone of the formula (VIII)

(VIII)

where the radicals $R^{22}$ and $R^{23}$ can in each case be identical or different and are a branched or unbranched $C_1$- to $C_{12}$-alkyl radical or $C_7$- to $C_{12}$-aralkyl radical or a $C_6$- to $C_{10}$-aryl radical or a $C_1$- to $C_6$-alkoxycarbonyl radical, where the specified radicals can in each case have one or more, preferably 1 to 3, identical or different substituents selected from the group $OR^{10e}$, $SR^{10f}$, $NR^{8e}R^{9e}$ and halogen, and where $R^{22}$ and $R^{23}$ can together also form a 5- to 8-membered ring which can have one or more ethylene double bonds and one or more identical or different hetero atoms selected from the group O, S, $NR^{11b}$, and where $R^{10e}$, $R^{10f}$, $R^{8e}$, $R^{9e}$ and $R^{11b}$ can have the meanings given above for $R^{11}$.

Alternatively to said carbonyl compounds, it is also possible to use vinyl ethers of the general formula (IX)

(IX)

within the scope of the method according to the invention, where the radicals $R^{24}$, $R^{25}$, $R^{26}$ and $R^{27}$, independently of one another, can in each case be identical or different and are a branched or unbranched $C_1$- to $C_{12}$-alkyl radical or $C_7$- to $C_{12}$-aralkyl radical or a $C_6$- to $C_{10}$-aryl radical, where the specified radicals can in each case have one or more, preferably 1 to 3, identical or different substituents selected from the group oxo, $OR^{10e}$, $SR^{10f}$, $NR^{8e}R^{9e}$ and halogen and where $R^{25}$ and $R^{26}$ can together also form a 5- to 8-membered ring which can have one or more ethylenic double bonds and one or more, usually 1 or 2, identical or different hetero atoms selected from the group O, S, $NR^{11b}$ and where $R^{10e}$, $R^{10f}$, $R^{8e}$, $R^{9e}$ and $R^{11b}$ can have the meanings given above for $C_1$- to $C_{12}$-Alkyl here is an above-described $C_1$- to $C_6$-alkyl and, moreover, is, for example, heptyl, octyl, nonyl, decyl, undecyl or dodecyl. In cases where two alkyl radicals together form a ring, alkyl radicals are also to be understood as alkylenyl radicals. $C_7$- to $C_{12}$-Aralkyl radicals and $C_6$- to $C_{10}$-aryl radicals can, for example, be attributed the abovementioned meanings. By way of example, $C_1$- to $C_6$-alkoxycarbonyl radicals which may be mentioned are: methoxycarbonyl, ethoxycarbonyl, propoxycarbonyl and isopropoxycarbonyl, preferably methoxycarbonyl and ethoxycarbonyl.

Within the scope of a preferred embodiment, the cyclization method according to the invention is carried out in the presence of a carboxylic acid anhydride of the formula (VI), where the radicals $R^{20}$ and $R^{20'}$ are identical and are a branched or unbranched $C_1$- to $C_{12}$-alkyl radical or $C_7$- to $C_{12}$-aralkyl radical or a $C_6$- to $C_{10}$-aryl radical, and where $R^{20}$ and $R^{20'}$ can together also form a 5- to 8-membered ring which can have one or more ethylenic double bonds and one or more identical or different hetero atoms selected from the group $OR^{10e}$, $SR^{10f}$, $NR^{11b}$, and $R^{10e}$, $R^{10f}$ and $R^{11b}$, independently of one another, can have the meanings given above for $R^{11}$.

Particular preference is given to using those carboxylic acid anhydrides in which the radicals $R^{20}$ and $R^{20'}$ are identical and are a branched or unbranched $C_1$- to $C_{12}$-alkyl radical or a $C_6$- to $C_{10}$-aryl radical. By way of example, carboxylic acid anhydrides which are to be used particularly preferably according to the invention are: acetic anhydride, propionaldehyde, pivalic anhydride and benzoic anhydride.

Aldehydes of the formula (VII) which can likewise preferably be used according to the invention are, for example, acetaldehyde, propionaldehyde and chloral (trichloroacetaldehyde).

If the cyclization method according to the invention is carried out within the scope of a further preferred embodiment in the presence of a ketone of the formula (VIII), it is advantageous to use those with an activated, i.e. low-electron, carbonyl function. By way of example, mention may be made of the following ketones, which are suitable to a particular degree for use within the scope of the method according to the invention: 1,1,1-trifluoroacetone, 1,1,1-trifluoroacetophenone, hexafluoroacetone, methyl pyruvate and ethyl pyruvate.

Vinyl ethers of the formula (IX) which can likewise preferably be used according to the invention are, for example: methyl vinyl ether, ethyl vinyl ether, isobutyl vinyl ether and 3,4-dihydro-2H-pyran.

The specified classes of compound can be used equally with good success within the scope of this preferred embodiment of the method according to the invention. With regard to practical aspects, such as, for example, a higher reaction rate, the use of aldehydes and/or low-electron ketones has proven to be advantageous.

The amount of carboxylic acid anhydride, aldehyde, ketone and/or vinyl ether to be used according to the invention can be varied within wide limits and is governed by the type of substance used and the degree of purity or the presence of impurities which are as yet not more precisely identified. Usually, the specified compounds and mixtures thereof are used in an amount of from about 0.01 mol % to about 5 mol %, preferably from about 0.1 mol % to about 2 mol %, based on the amount of citronelial used.

The type and manner of the reaction procedure, for example the configuration of reactors or the order in which individual reactants are added, are not subject to particular requirements provided a reaction procedure with extensive exclusion of oxygen and water is ensured.

To carry out the method according to the invention within the scope of this preferred embodiment, the procedure advantageously involves firstly providing a solution of the diarylphenoxyaluminum compound to be used according to the invention in a suitable solvent, as described above. Then, in accordance with the invention, a mixture of the racemic or nonracemic citronellal to be cyclized with the selected carboxylic acid anhydride, the aldehyde, the activated ketone and/or the vinyl ether is preferably added to this solution. Alternatively, it is possible, for example, to also admix the solution of the diarylphenoxyaluminum compound to be used according to the invention firstly with the carboxylic acid anhydride, the aldehyde, the ketone and/or the vinyl ether selected, if appropriate, in each case, and to afterwards add the citronellal to be cyclized.

It has proven to be advantageous to meter in the citronellal or the mixture of citronellal with the selected compound to the catalyst solution or to the reaction mixture within a period of from about 30 min to about 6 h, preferably within about 2 h to about 4 h. The citronella can here be added as it is or in the form of a solution, advantageously in one of the abovementioned suitable solvents. Within the scope of an in turn preferred embodiment of the method according to the invention, a solution of the selected ligand of the formulae (I) or (Ia) in toluene is firstly prepared and then, expediently with stirring, the selected aluminum compound of the formula (II) and/or (III), preferably trimethyl-aluminum or triethylaluminum in toluenic solution is added.

The addition of the citronellal to be cyclized or the mixture of citronellal with the selected carboxylic acid anhydride, aldehyde, activated ketone and/or the vinyl ether takes place within the scope of this embodiment advantageously at temperatures in the range from about −40° C. to about 40° C., preferably in the range from about −20° C. to about 20° C. For this, the prepared solution or suspension of the diarylphenoxyaluminum compound according to the invention is advantageously cooled to a temperature in this range, e.g. to a temperature in the range from −10° C. to 10° C., and the other reactants are added in precooled form.

The addition of the mixture of citronellal and of the selected further compound can be undertaken such that either the total amount of citronellal is added in one portion or is added to the prepared catalyst solution in portions or else continuously. Suitable solvents are in turn preferably the abovementioned solvents, in particular toluene. Preference is given to using the citronellal to be cyclized in the form of a mixture with the selected carboxylic acid anhydride, aldehyde, activated ketone and/or vinyl ether without the further addition of solvents. When using a solvent, the total amount of solvent is advantageously chosen so that the volume-based ratio of citronellal to be reacted relative to the solvent is about 1:1 to about 1:20, preferably from about 1:1 to about 1:10.

It has been found that some of the catalyst complex is usually deactivated during the reaction. This is to be attributed, inter alia, to ligand-exchange processes between the bis(diarylphenol) ligands of the formula used in each case of the diarylphenoxyaluminum compounds used and the isopulegol which forms as a result of cyclization. In contrast to the active polymeric catalyst, the deactivated form of the catalyst is usually soluble in the reaction mixture, depending on the choice of solvents used.

In a preferred embodiment, simple physical separation methods (e.g. filtration or centrifugation of the still-active catalyst) can be used to separate off the deactivated part of the catalyst together with the rest of the reaction mixture. The retained, still-active part of the catalyst can, if desired, be topped up with fresh catalyst and be reused with negligible loss in activity, preferably in the course of a further cyclization reaction according to the invention of citronellal to isopulegol.

Alternatively, the amount of catalyst used can be chosen so that the total catalyst complex used is deactivated in the course of the cyclization reaction according to the invention, or after completion of said reaction, and is thus soluble, which can be seen from a clear reaction mixture. In this connection, it is advantageously noticeable that in this case, on account of the above-described ligand-exchange processes, the bis(diarylphenoxy) ligand of the formula (I) used in each case is released without having to carry out separate hydrolysis.

Moreover, it has been found that, following distillative removal of the solvent used in each case, preferably of the toluene, and of the further compound used if appropriate, the cyclization product isopulegol can be distilled off from the reaction mixture in high purities without prior hydrolysis of the diarylphenoxyaluminum compounds used in each case. In this connection, no recognizable undesired or troublesome by-products usually form in the distillation bottom either. Adding a suitable, inert high-boiling solvent, i.e. preferably a solvent which has a higher boiling point than isopulegol, such as, for example, 1-methylnaphthalene, 1-decanol, tridecane, 1,2-propylenecarbonate, diethylene glycol dibutyl ether, tetraethylene glycol dimethyl ether and dibenzyl ether, before the distillation gives, in the distillation bottom, a solution of the free ligand in the hot high-boiling component used in each case. The ligand can be crystallized out from this hot solution by simple cooling and be recovered in high purity by filtration. The bis(diarylphenoxy) ligand recovered in this way can, usually without further purification steps, be reacted in the course of a new batch with the corresponding aluminum compounds of the formulae (II) or (III) to give the reactive catalyst complex, where, in the case of catalyst complexes recovered in this way, no or only negligible weakening of the reactivity is established. Moreover, further amounts of isopulegol and the bis(diarylphenoxy) ligand used in each case can be obtained, following hydrolysis, from the mother liquor obtained as residue of the above-described. Within the scope of this preferred embodiment, the cyclization method according to the invention of citronellal to isopulegol correspondingly comprises the following steps.

a) distillative removal of the solvent used, if appropriate, and of the further compound used, if appropriate, (i.e. the carboxylic acid anhydride, aldehydes, ketones and/or vinyl ethers) from the product mixture obtained according to the method described above, b) addition of a high-boiling solvent to the residue obtained in step a), c) distillative separation of the isopulegol from the mixture obtained in step b) and d) cooling of the distillation bottom obtained in step c) with crystallization of the bis(diarylphenol) ligand of the formula (I) used.

After the desired reaction progress has been achieved, the cyclization reaction according to the invention can also be terminated in the usual manner, for example by adding an aqueous reagent, for example an aqueous alkaline solution, such as, for example, sodium or potassium hydroxide solution or, for example, also by adding water. The work-up and isolation can then be carried out in the manner known per se to the person skilled in the art.

The additive used if appropriate, i.e. the carboxylic acid anhydride, ketone or aldehyde or vinyl ether used, can be recovered depending on its physical properties (e.g. the boiling point) e.g. by distillation from the fully reacted mixture extensively and to a degree in which it has not, if appropriate, even been reacted.

In the course of the method according to the invention, isopulegol is usually obtained in the form of a mixture of the diastereomeric forms of isopulegol: isopulegol of the formula (XIII), neo-isopulegol of the formula (XIV), neoiso-isopulegol of the formula (XV) and iso-isopulegol of the formula (XVI).

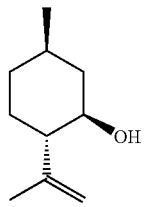

(XIII)

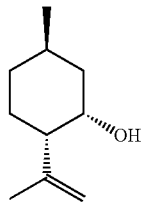

(XIV)

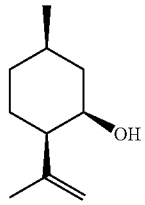

(XV)

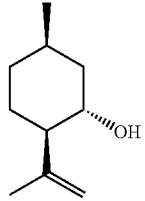

(XVI)

According to the invention, preference is given to embodiments of the method according to the invention in which a diastereomer mixture of isopulegol is produced which itself consists of at least about 85%, preferably of at least about 90% and particularly preferably of at least about 95% and very particularly preferably of at least about 98%, of the main diastereomer isopulegol of the formula (XII) or of the formula (IVa).

The method according to the invention is equally suitable, as already mentioned, for cyclizing racemic and also nonracemic, i.e. optically active, citronellal to give racemic and nonracemic isopulegol. In a preferred embodiment, the method according to the invention serves for producing L-(−)-isopulegol by cyclization of D-(+)-citronellal.

The racemic and nonracemic isopulegol produced in this way represents a valuable intermediate for producing racemic or nonracemic menthol, one of the most significant fragrances or aromas worldwide. Menthol can be obtained from isopulegol by methods of hydrogenation known per se to the person skilled in the art, especially catalytic hydrogenation over suitable transition metal catalysts, as described, for example, in Pickard et al., J. Chem. Soc. 1920, 1253; Ohloff et al., Chem. Ber. 1962, 95, 1400; Pavia et al., Bull. Soc. Chim. Fr. 1981, 24, Otsuka et al., Synthesis 1991, 665 or in EP 1 053 974 A. Here, if the chosen reaction conditions are suitable, the relative or absolute configuration of the isopulegol used is largely retained, and in many cases is completely retained.

The present invention therefore also relates to a method of producing racemic or nonracemic menthol starting from racemic or nonracemic isopulegol produced by the method described above and subsequent hydrogenation of its ethylenic double bond. In particular, the present invention relates to a method of producing L-(−)-menthol starting from L-(−)-isopulegol produced by the method described above by cyclization according to the invention of D-(+)-citronellal.

The following examples serve to illustrate the invention without limiting it in any way:

Gas-chromatographic analyses were carried out by the following method:

30 m DB-WAX, ID.: 0.32 mm, FD.: 0.25 μm; 80–230° C., 3° C./min; Rf (citronellal): 10.5; Rf (neo-isopulegol): 13.24;

A heat-dried flask was charged with 1.05 mmol of the ligand $Ia_1$-1 and 10 ml of anhydrous toluene. At room temperature, 350 μl (0.66 mmol, 1 mol %) of a 25% strength solution of triethylaluminum in toluene were added to the clear solution. The solution was stirred for 1 h at 25° C. After a few minutes, a gel-like suspension of the catalyst was obtained. The catalyst suspension was cooled to 0° C., and a mixture of 10.15 g (65.8 mmol) of citronellal precooled to 0° C. and 1% by weight (based on citronellal) of acetic anhydride was added over a period of 6 h. The reaction mixture was stirred, and samples were taken at regular intervals and hydrolyzed with 8% strength NaOH. During this, the aluminum present precipitated out as hydroxide and a suspension was firstly obtained. After some time, two clear phases formed. The organic phase was analyzed by gas chromatography. The results are shown in table 4:

TABLE 4

| Time in h | Citronellal added in g | Citronellal in % by wt. | Citronellal in g | Isopulegol in % by wt. | Isopulegol in g | Citronellol in % by wt. | Citronellol in g | Ester* in % by wt. | Ester* in g |
|---|---|---|---|---|---|---|---|---|---|
| 1 | 2.03 | 83.15 | 1.69 | 13.00 | 0.26 | | 0.00 | | 0.00 |
| 2 | 4.06 | 59.55 | 2.42 | 33.04 | 1.34 | 0.44 | 0.02 | 0.72 | 0.03 |
| 3 | 6.09 | 54.43 | 3.31 | 37.17 | 2.26 | 0.49 | 0.03 | 0.79 | 0.05 |
| 4 | 8.12 | 49.48 | 4.02 | 42.54 | 3.45 | 0.48 | 0.04 | 0.79 | 0.06 |
| 5 | 10.15 | 46.33 | 4.70 | 45.50 | 4.62 | 0.46 | 0.05 | 0.67 | 0.07 |
| 6 | 10.15 | 32.08 | 3.26 | 59.70 | 6.06 | 0.47 | 0.05 | 0.73 | 0.07 |
| 72 | 10.15 | 0.25 | 0.03 | 89.60 | 9.09 | 0.89 | 0.09 | 0.78 | 0.08 |

*Citronellyl citronellate

Rf (isopulegol): 13.58; Rf (neoiso-isopulegol): 14.64; Rf (iso-isopulegol) 15.28; Mf (citronellyl citronellate): 39.80. Concentrations of the resulting reaction products in the reaction solution (in each case in % by weight) were ascertained by GC analysis using an internal standard. The additionally stated corresponding mass data (in each case in g) were extrapolated therefrom by calculation and can therefore have slight deviations. Diastereoselectivities were ascertained from the respective GC area % of the four diastereomers.

EXAMPLE 1

Cyclization of Citronella to Isopulegol in the Presence of a Catalyst Produced from the Ligand $Ia_1$-1 and in the Presence of Acetic Anhydride

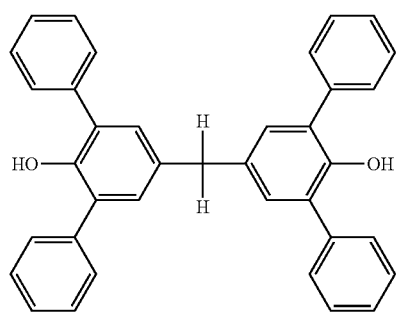

$Ia_1$-1

The cyclization reaction produced isopulegol with a selectivity of 90% based on all isopulegol isomers. The diastereoselectivity (neo-isopulegol:isopulegol:neoiso-isopulegol:iso-isopulegol) was 0.4:99.4:0.2:0.0.

EXAMPLE 2

Cyclization Using the Ligand $Ia_1$-4 (with Acetic Anhydride)

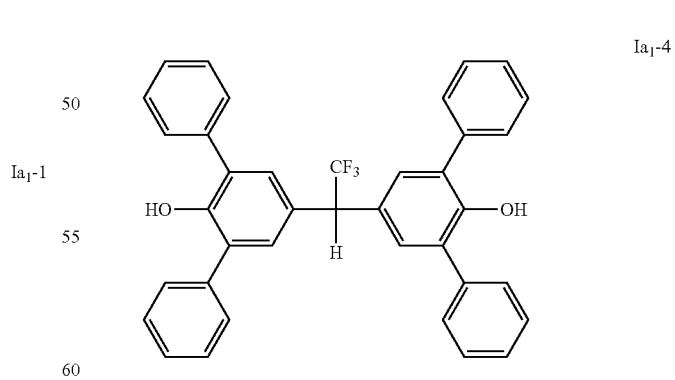

$Ia_1$-4

Example 1 was repeated using the ligand $Ia_1$-4 (on a larger scale) under otherwise unchanged conditions. The results are shown in table 5.

TABLE 5

| Time in h | Citronellal added in g | Citronellal in % by wt. | Citronellal in g | Isopulegol in % by wt. | Isopulegol in g | Citronellol in % by wt. | Citronellol in g |
|---|---|---|---|---|---|---|---|
| 2 | 16.92 | 26.54 | 4.49 | 63.00 | 10.66 | 1.63 | 0.28 |
| 3 | 25.38 | 24.23 | 6.15 | 65.87 | 16.72 | 1.53 | 0.39 |
| 4 | 33.83 | 19.14 | 6.48 | 72.54 | 24.54 | 1.40 | 0.47 |
| 5 | 42.29 | 17.66 | 7.47 | 74.80 | 31.63 | 1.20 | 0.51 |
| 6 | 50.75 | 19.73 | 10.01 | 73.22 | 37.16 | 1.04 | 0.53 |
| 7 | 50.75 | 11.97 | 6.07 | 80.51 | 40.86 | 1.02 | 0.52 |
| 24 | 50.75 | 1.24 | 0.63 | 90.11 | 45.73 | 0.96 | 0.49 |

After a reaction time of 24 h, the conversion of citronellal was complete with a selectivity of 90% with regard to all isopulegol isomers. The diastereoselectivity (neo isopulegol:isopulegol:neoiso-isopulegol:iso-isopulegol) was 0.6:99.0:0.3:0.1.

Example 3
Cyclization Using the Ligand $Ia_2$-1 (without Additives)

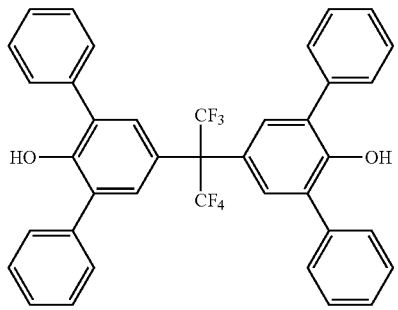

$Ia_2$-1

A heat-dried flask was charged with 640 mg (1.0 mmol) of the ligand $Ia_2$-1 and 10 ml of anhydrous toluene. At room temperature, 350 µl (0.65 mmol, 1 mol % with regard to citronellal) of a 0.66 M solution of triethylaluminum in toluene were added to the clear solution. The solution was stirred for 1 h at 25° C., giving a gel-like suspension of the catalyst after a few minutes. The catalyst suspension was cooled to 0° C., and 10.2 g (65.8 mmol) of −15° C.-cold citronellal were added over a period of 6 h. The reaction mixture was stirred for a further 18 h at 0° C., and samples were taken at regular intervals and hydrolyzed with 8% strength NaOH. During this, the aluminum present precipitated out as hydroxide and a suspension was firstly obtained. After some time, two clear phases formed. The organic phase was analyzed by gas chromatography, The results are shown in table 6:

TABLE 6

| Time in h | Citronellal added in g | Citronellal in % by wt. | Citronellal in g | Isopulegol in % by wt. | Isopulegol in g | Citronellol in % by wt. | Citronellol in g | Ester* in g/100 g per GC | Ester* in g |
|---|---|---|---|---|---|---|---|---|---|
| 2 | 3.38 | 6.01 | 0.75 | 17.34 | 2.17 | 0.23 | 0.00 | — | — |
| 3 | 5.08 | 9.13 | 1.30 | 21.54 | 3.06 | 0.34 | 0.01 | — | — |
| 4 | 6.77 | 14.48 | 2.30 | 22.32 | 3.54 | 0.55 | 0.02 | 0.31 | 0.05 |
| 5 | 8.46 | 18.88 | 3.32 | 24.35 | 4.28 | 0.77 | 0.03 | 0.68 | 0.12 |
| 6 | 10.15 | 24.94 | 4.80 | 24.38 | 4.70 | 1.03 | 0.05 | 1.34 | 0.26 |
| 7 | 10.15 | 24.23 | 4.67 | 25.49 | 4.91 | 1.16 | 0.06 | 1.67 | 0.32 |
| 24 | 10.15 | 13.80 | 2.66 | 26.82 | 5.17 | 3.08 | 0.16 | 11.19 | 2.16 |

*Citronellyl citronellate

The diastereomer ratio (neo-isopulegol:isopulegol:neoiso-isopulegol:iso-isopulegol) was 1.6:96.7:1.2:0.4.

EXAMPLE 4

Cyclization Using the Ligand Ia$_2$-1 (with Acetic Anhydride)

A heat-dried flask was charged with 640 mg (1.0 mmol) of the ligand Ia$_2$-1 and 10 ml of anhydrous toluene. At room temperature, 350 μl (0.65 mmol, 1 mol % with regard to citronellal) of a 0.66 M solution of triethylaluminum in toluene were added to the clear solution. The solution was stirred for 1 h at 25° C., giving a gel-like suspension of the catalyst after a few minutes. The catalyst suspension was cooled to 0° C., and a mixture of 10.2 g (65.8 mmol) of −15° C.-cold citronellal and 0.1 g (1% by weight with regard to citronellal) of acetic anhydride was added over a period of 6 h. The reaction mixture was stirred for a further 18 h at 0° C., and samples were taken at regular intervals and hydrolyzed with 8% strength NaOH. During this, the aluminum present precipitated out as hydroxide and a suspension was firstly obtained. After some time, two clear phases formed The organic phase was analyzed by gas chromatography. The results are shown in table 7:

mmol) of a 25% strength triethylaluminum solution in toluene were added and the mixture was after-stirred for 1 h. The resulting catalyst suspension was cooled to 0° C. and, over the course of 5 h, a mixture of 70.0 g (0.45 mol) of citronellal and 0.7 g (6.86 mmol, 1% by weight with regard to citronellal) of acetic anhydride was added. The mixture was after-stirred for 1 h at 0° C. and for 12 h at room temperature. At the end of the experiment, 100 ml of 8% strength sodium hydroxide solution were added and the phases separated. The organic phase was dried with sodium sulfate and the solvent was removed under reduced pressure. The crude product was distilled at 1 mbar over a short column. At a top temperature of 58° C., 68.4 g of isopulegol with the following composition (in each case GC area %) were obtained: isopulegol: 98.4%, neo-isopulegol: 0.6%, neoiso-isopulegol: 0.4%. This corresponds to a chemical yield of 97%, based on all diastereomers and a diastereoselectivity of 99:1 (isopulegol: other diastereomers).

The distillation bottom which remains when distillation is complete was a pale yellow solid in an amount of 7.7 g, which consisted of 95% by weight of the ligand of the formula Ia$_2$-3 used and of 5% by weight of isopulegol.

TABLE 7

| Time in h | Citronellal added in g | Citronellal in g/100 g | Citronellal in g | Isopulegol in g/100 g | Isopulegol in g | Citronellol g/100 g | Citronellol in g | Ester* in g/100 g | Ester* in g |
|---|---|---|---|---|---|---|---|---|---|
| 2 | 3.38 | 11.76 | 1.47 | 22.32 | 2.79 | 0.00 | 0.00 | 0.00 | 0.00 |
| 3 | 5.08 | 12.34 | 1.75 | 28.08 | 3.98 | 0.00 | 0.00 | 0.00 | 0.00 |
| 4 | 6.77 | 14.61 | 2.32 | 27.54 | 4.37 | 0.00 | 0.00 | 0.00 | 0.00 |
| 5 | 8.46 | 18.78 | 3.30 | 32.93 | 5.79 | 0.00 | 0.00 | 0.00 | 0.00 |
| 6 | 10.15 | 22.01 | 4.24 | 32.98 | 6.35 | 0.00 | 0.00 | 0.00 | 0.00 |
| 7 | 10.15 | 16.11 | 3.10 | 40.16 | 7.73 | 0.00 | 0.00 | 0.00 | 0.00 |
| 24 | 10.15 | 2.11 | 0.41 | 51.56 | 9.93 | 0.09 | 0.02 | 0.00 | 0.00 |

*Citronellyl citronellate

The diastereomer ratio (neo-isopulegol:isopulegol:neoiso-isopulegol:iso-isopulegol) was 0.8:98.5:0.4:0.3.

EXAMPLE 5

Cyclization of Citronellal in the Presence of a Catalyst Produced from the Ligand Ia$_2$-3 and in the Presence of Acetic Anhydride with Subsequent Work-Up and Recovery of the Ligand

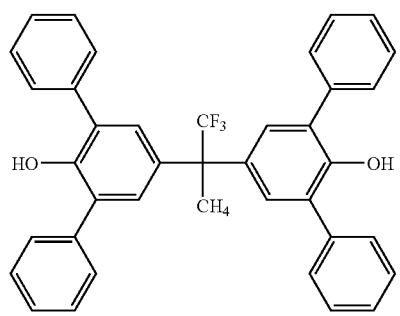

Ia$_2$-3

8.0 g (13.6 mmol) of the ligand Ia$_2$-3 were dissolved in 140 ml of toluene at room temperature under argon. 4.78 ml (9.09

EXAMPLES 6-13

Cyclization of Citronellal Using Various Carbonyl Compounds as Additives in the Cyclization Using the Ligand Ia$_2$-3

EXAMPLE 6

Cyclization without Additive

A heat-dried flask was charged with 580 mg (1.0 mmol) of the ligand Ia$_2$-3 and 20 ml of anhydrous toluene. At room temperature, 350 μl (0.65 mmol, 1 mol % with regard to citronellal) of a 0.66 M solution of triethylaluminum in toluene were added to the clear solution. The solution was stirred for 1 h at 25° C., giving a gel-like suspension of the catalyst after a few minutes. The catalyst suspension was cooled to 0° C., and 10.2 g (65.8 mmol) of −15° C.-cold citronellal were added over a period of 3 h. The reaction mixture was stirred for a further 4 h at 0° C., and samples were taken at regular intervals and hydrolyzed with 8% strength NaOH. During this, the aluminum present precipitated out as hydroxide and a suspension was initially obtained. After some time, two clear phases formed. The organic phase was analyzed by gas chromatography. The results are shown in table 8:

TABLE 8

| Time in h | Citronellal added in g | Citronellal in % by wt. | Citronellal in g | Isopulegol in % by wt. | Isopulegol in g | Citronellol in % by wt. | Citronellol in g | Ester* in % by wt. | Ester* in g |
|---|---|---|---|---|---|---|---|---|---|
| 1 | 2.54 | 8.40 | 1.74 | 7.13 | 1.48 | 0.08 | 0.02 | 0.34 | 0.07 |
| 2 | 5.08 | 10.43 | 2.43 | 13.77 | 3.21 | 0.16 | 0.04 | 0.65 | 0.15 |
| 3 | 7.61 | 11.85 | 3.06 | 21.54 | 5.56 | 0.23 | 0.06 | 0.64 | 0.17 |
| 4 | 10.15 | 16.99 | 4.82 | 24.55 | 6.96 | 0.24 | 0.07 | 0.51 | 0.14 |
| 5 | 10.15 | 10.66 | 3.02 | 31.15 | 8.83 | 0.32 | 0.09 | 0.57 | 0.16 |
| 6 | 10.15 | 4.73 | 1.34 | 36.26 | 10.28 | 0.40 | 0.11 | 0.62 | 0.18 |
| 7 | 10.15 | 2.92 | 0.83 | 38.30 | 10.86 | 0.39 | 0.11 | 0.63 | 0.18 |

*Citronellyl citronellate

The diastereomer ratio (neo-isopulegol:isopulegol:neoiso-isopulegol:iso-isopulegol) was 0.4:99.0:0.5:0.1.

EXAMPLE 7

Addition of Acetaldehyde

The experiment was repeated as in example 6 except that 0.4% by weight of acetaldehyde was added to the citronellal prior to it being added. The results are shown in table 9:

TABLE 9

| Time in h | Citronellal added in g | Citronellal in % by wt. | Citronellal in g | Isopulegol in % by wt. | Isopulegol in g | Citronellol in % by wt. | Citronellol in g | Ester* in % by wt. | Ester* in g |
|---|---|---|---|---|---|---|---|---|---|
| 1 | 2.54 | 10.27 | 2.13 | 6.56 | 1.36 | 0.10 | 0.02 | 0.35 | 0.07 |
| 2 | 5.08 | 12.53 | 2.92 | 13.73 | 3.20 | 0.13 | 0.03 | 0.28 | 0.07 |
| 3 | 7.61 | 13.51 | 3.49 | 20.45 | 5.28 | 0.15 | 0.04 | 0.27 | 0.07 |
| 4 | 10.15 | 12.34 | 3.50 | 26.87 | 7.62 | 0.26 | 0.07 | 0.28 | 0.08 |
| 5 | 10.15 | 6.84 | 1.94 | 32.05 | 9.09 | 0.30 | 0.09 | 0.31 | 0.09 |
| 6 | 10.15 | 3.45 | 0.98 | 35.33 | 10.02 | 0.33 | 0.09 | 0.31 | 0.09 |
| 7 | 10.15 | 1.62 | 0.46 | 36.88 | 10.46 | 0.36 | 0.10 | 0.32 | 0.09 |

*Citronellyl citronellate

The diastereomer ratio (neo-isopulegol:isopulegol:neoiso-isopulegol:iso-isopulegol) was 0.4:99.1:0.5:0.0.

EXAMPLE 8

Addition of Nitrobenzaldehyde

The experiment was repeated as in example 6 except that 1.3% by weight of nitrobenzaldehyde were added to the citronellal prior to it being added. The results are shown in table 10:

TABLE 10

| Time in h | Citronellal added in g | Citronellal in % by wt. | Citronellal in g | Isopulegol in % by wt. | Isopulegol in g | Citronellol in % by wt. | Citronellol in g | Ester* in % by wt. | Ester* in g |
|---|---|---|---|---|---|---|---|---|---|
| 1 | 2.54 | 7.48 | 1.55 | 7.17 | 1.49 | 0.16 | 0.03 | 0.96 | 0.20 |
| 2 | 5.08 | 9.14 | 2.13 | 13.26 | 3.09 | 0.17 | 0.04 | 0.61 | 0.14 |
| 3 | 7.61 | 10.09 | 2.60 | 21.11 | 5.45 | 0.21 | 0.05 | 0.48 | 0.12 |
| 4 | 10.15 | 11.32 | 3.21 | 27.72 | 7.86 | 0.25 | 0.07 | 0.38 | 0.11 |
| 5 | 10.15 | 6.54 | 1.85 | 32.78 | 9.29 | 0.27 | 0.08 | 0.40 | 0.11 |
| 6 | 10.15 | 2.35 | 0.67 | 36.54 | 10.36 | 0.31 | 0.09 | 0.42 | 0.12 |
| 7 | 10.15 | 1.30 | 0.37 | 37.55 | 10.65 | 0.31 | 0.09 | 0.42 | 0.12 |

*Citronellyl citronellate

The diastereomer ratio (neo-isopulegol:isopulegol:neoiso-isopulegol:iso-isopulegol) was 0.4:99.2:0.4:0.0.

EXAMPLE 9

Addition of Chloral

The experiment was repeated as in example 6 except that 1.3% by weight of anhydrous chloral were added to the citronellal prior to it being added. The results are shown in table 11:

TABLE 11

| Time in h | Citronellal added in g | Citronellal in % by wt. | Citronellal in g | Isopulegol in % by wt. | Isopulegol in g | Citronellol in % by wt. | Citronellol in g | Ester* in % by wt. | Ester* in g |
|---|---|---|---|---|---|---|---|---|---|
| 1 | 2.54 | 4.49 | 0.93 | 9.85 | 2.04 | 0.00 | 0.00 | 0.00 | 0.00 |
| 2 | 5.08 | 5.09 | 1.18 | 17.69 | 4.12 | 0.00 | 0.00 | 0.00 | 0.00 |
| 3 | 7.61 | 6.05 | 1.56 | 26.45 | 6.83 | 0.00 | 0.00 | 0.00 | 0.00 |
| 4 | 10.15 | 8.02 | 2.27 | 31.63 | 8.97 | 0.00 | 0.00 | 0.00 | 0.00 |
| 5 | 10.15 | 3.00 | 0.85 | 37.38 | 10.60 | 0.00 | 0.00 | 0.00 | 0.00 |
| 6 | 10.15 | 1.22 | 0.35 | 39.17 | 11.10 | 0.00 | 0.00 | 0.00 | 0.00 |
| 7 | 10.15 | 0.56 | 0.16 | 39.63 | 11.24 | 0.00 | 0.00 | 0.00 | 0.00 |

*Citronellyl citronellate

The diastereomer ratio (neo-isopulegol:isopulegol:neoiso-isopulegol:iso-isopulegol) was 0.5:99.3:0.2:0.0.

EXAMPLE 10

Addition of Ethyl Pyruvate

The experiment was repeated as in example 6 except that 1.0% by weight of ethyl pyruvate was added to the citronellal prior to it being added. The results are shown in table 12:

TABLE 12

| Time in h | Citronellal added in g | Citronellal in % by wt. | Citronellal in g | Isopulegol in % by wt. | Isopulegol in g | Citronellol in % by wt. | Citronellol in g | Ester* in % by wt. | Ester* in g |
|---|---|---|---|---|---|---|---|---|---|
| 1 | 2.54 | 8.84 | 1.83 | 6.51 | 1.35 | 0.00 | 0.00 | 0.00 | 0.00 |
| 2 | 5.08 | 14.47 | 3.37 | 9.28 | 2.16 | 0.00 | 0.00 | 0.00 | 0.00 |
| 3 | 7.61 | 18.07 | 4.66 | 13.77 | 3.55 | 0.00 | 0.00 | 0.00 | 0.00 |
| 4 | 10.15 | 18.98 | 5.38 | 19.69 | 5.58 | 0.00 | 0.00 | 0.00 | 0.00 |
| 5 | 10.15 | 13.94 | 3.95 | 25.09 | 7.11 | 0.00 | 0.00 | 0.00 | 0.00 |
| 6 | 10.15 | 9.93 | 2.82 | 28.64 | 8.12 | 0.00 | 0.00 | 0.00 | 0.00 |
| 7 | 10.15 | 7.14 | 2.02 | 31.27 | 8.87 | 0.00 | 0.00 | 0.00 | 0.00 |

*Citronellyl citronellate

The diastereomer ratio (neo-isopulegol:isopulegol:neoiso-isopulegol:iso-isopulegol) was 0.5:99.5:0.0:0.0.

EXAMPLE 11

Addition of Trifluoroacetone

The experiment was repeated as in example 6 except that 1.0% by weight of 1,1,1-trifluoroacetone was added to the citronellal prior to it being added. The results are shown in table 13:

TABLE 13

| Time in h | Citronellal added in g | Citronellal in % by wt. | Citronellal in g | Isopulegol in % by wt. | Isopulegol in g | Citronellol in % by wt. | Citronellol in g | Ester* in % by wt. | Ester* in g |
|---|---|---|---|---|---|---|---|---|---|
| 1 | 2.54 | 8.95 | 1.86 | 5.46 | 1.13 | 0.09 | 0.02 | 0.00 | 0.00 |
| 2 | 5.08 | 11.27 | 2.62 | 12.43 | 2.89 | 0.14 | 0.03 | 0.37 | 0.09 |

TABLE 13-continued

| Time in h | Citronellal added in g | Citronellal in % by wt. | Citronellal in g | Isopulegol in % by wt. | Isopulegol in g | Citronellol in % by wt. | Citronellol in g | Ester* in % by wt. | Ester* in g |
|---|---|---|---|---|---|---|---|---|---|
| 3 | 7.61 | 12.73 | 3.29 | 20.60 | 5.32 | 0.16 | 0.04 | 0.31 | 0.08 |
| 4 | 10.15 | 11.93 | 3.38 | 28.31 | 8.03 | 0.17 | 0.05 | 0.24 | 0.07 |
| 5 | 10.15 | 4.26 | 1.21 | 35.89 | 10.17 | 0.20 | 0.06 | 0.25 | 0.07 |
| 6 | 10.15 | 0.44 | 0.12 | 38.44 | 10.90 | 0.20 | 0.06 | 0.24 | 0.07 |
| 7 | 10.15 | 0.16 | 0.05 | 39.61 | 11.23 | 0.20 | 0.06 | 0.25 | 0.07 |

*Citronellyl citronellate

The diastereomer ratio (neo-isopulegol:isopulegol:neoiso-isopulegol:iso-isopulegol) was 0.8:98.9:0.3:0.0.

EXAMPLE 12

The experiment was repeated as in example 6 with a sample of crude citronellal (with increased citronellol content) produced by hydrogenation. The results are shown in table 14:

TABLE 14

| Time in h | Citronellal added in g | Citronellal in % by wt. | Citronellal in g | Isopulegol in % by wt. | Isopulegol in g | Citronellol in % by wt. | Citronellol in g | Ester* in % by wt. | Ester* in g |
|---|---|---|---|---|---|---|---|---|---|
| 1 | 2.54 | 11.48 | 2.38 | 2.94 | 0.61 | 0.32 | 0.07 | 6.86 | 1.42 |
| 2 | 5.08 | 17.03 | 3.96 | 6.40 | 1.49 | 0.53 | 0.12 | 6.72 | 1.56 |
| 3 | 7.61 | 17.42 | 4.50 | 11.33 | 2.92 | 1.06 | 0.27 | 9.93 | 2.56 |
| 4 | 10.15 | 9.99 | 2.83 | 13.72 | 3.89 | 2.17 | 0.62 | 20.52 | 5.82 |
| 5 | 10.15 | 3.97 | 1.13 | 15.07 | 4.27 | 2.67 | 0.76 | 26.34 | 7.47 |
| 6 | 10.15 | 2.61 | 0.74 | 15.35 | 4.35 | 2.83 | 0.80 | 27.73 | 7.86 |
| 7 | 10.15 | 1.96 | 0.56 | 15.52 | 4.40 | 2.92 | 0.83 | 28.22 | 8.00 |

*Citronellyl citronellate

The diastereomer ratio (neo-isopulegol:isopulegol:neoiso-isopulegol:iso-isopulegol) was 0.5:99.5:0.0:0.0.

EXAMPLE 13

The experiment was repeated as in example 12 except that 1.0% by weight of 1,1,1-trifluoroacetone was added to the citronellal prior to it being added. The results are shown in table 15:

TABLE 15

| Time in h | Citronellal added in g | Citronellal in % by wt. | Citronellal in g | Isopulegol in % by wt. | Isopulegol in g | Citronellol in % by wt. | Citronellol in g | Ester* in % by wt. | Ester* in g |
|---|---|---|---|---|---|---|---|---|---|
| 1 | 2.54 | 6.20 | 1.29 | 7.10 | 1.47 | 0.18 | 0.04 | 0.1 | 0.021 |
| 2 | 5.08 | 9.83 | 2.29 | 13.71 | 3.19 | 0.08 | 0.02 | 0.11 | 0.026 |
| 3 | 7.61 | 11.18 | 2.89 | 21.55 | 5.56 | 0.09 | 0.02 | 0.15 | 0.039 |
| 4 | 10.15 | 11.33 | 3.21 | 28.61 | 8.11 | 0.10 | 0.03 | 0.17 | 0.048 |
| 5 | 10.15 | 3.26 | 0.92 | 37.46 | 10.62 | 0.10 | 0.03 | 0.19 | 0.054 |
| 6 | 10.15 | 0.85 | 0.24 | 39.48 | 11.19 | 0.10 | 0.03 | 0.20 | 0.057 |
| 7 | 10.15 | 0.17 | 0.05 | 40.00 | 11.34 | 0.09 | 0.03 | 0.19 | 0.054 |

*Citronellyl citronellate

The diastereomer ratio (neo-isopulegol:isopulegol:neoiso-isopulegol:iso-isopulegol) was 0.5:99.0:0.3:0.2.

EXAMPLE 14

Recovery of the Catalyst Complex with Ligand Ia$_2$-3

A heat-dried flask was charged with 2.93 g (4.99 mmol) of the ligand Ia$_2$-3 and 100 ml of anhydrous toluene. At room temperature, 1.75 ml (3.33 mmol, 5 mol % with regard to citronellal) of a 0.66 M solution of triethylaluminum in toluene were added to the clear solution. The solution was stirred for 1 h at 25° C., giving a gel-like suspension of the catalyst after a few minutes. The catalyst suspension was cooled to 0° C., and 10.2 g (65.8 mmol) of −15° C.-cold citronellal were added over a period of 1 h. The reaction mixture was stirred for a further hour at 0° C. The reaction mixture was separated from the solid catalyst by filtration. The filtrate was worked up as usual, the toluene was removed by distillation, and the resulting crude product was analyzed. The results are shown in table 16:

TABLE 16

| Citronellal added in g | Citronellal in % by wt. | Citronellal in g | Isopulegol in % by wt. | Isopulegol in g | Citronellol in % by wt. | Citronellol in g |
|---|---|---|---|---|---|---|
| 10.15 | 0.11 | 0.02 | 69.56 | 10.02 | 1.38 | 0.11 |

The filtered-off catalyst was suspended in a further 100 ml of toluene. The catalyst suspension produced in this way was cooled to 0° C., and 10.2 g (65.8 mmol) of −15° C.-cold citronellal were added over a period of 6 h. The reaction mixture was stirred for a further 18 h at 0° C. and then worked up and analyzed as usual. The results are shown in table 17:

EXAMPLE 15

Method to Recover the Ligand Ia$_2$-3

At room temperature 14 ml (26.4 mmol, 1 mol % with regard to citronellal) of a 0.66 M solution of triethylaluminum in toluene were added to a solution of 23.44 g (40 mmol) of the ligand Ia$_2$-3 in 800 ml of anhydrous toluene. The solution was stirred for 1 h at 25° C., giving a gel-like suspension of the catalyst after a few minutes. The catalyst suspension was cooled to 0° C., and a mixture of 406 g (2.64 mol) and 4.06 9 (1 mol % based on citronellal) of trifluoroacetone was cooled to −15° C. and added over a period of 3 h. The mixture was after-stirred for a further 4 h at 0° C., producing a clear solution.

The toluene was distilled off at atmospheric pressure over a 15 cm Vigreux column. 80 g of 1-methylnaphthalene were added as high-boiling component to the clear solution, and a total of 364 g of isopulegol were distilled off at 10 mbar. This corresponds to a yield of 87%. White crystals crystallized out of the bottom upon cooling. Filtration gave a total of 20.0 g of a white solid, which could be identified by analysis as ligand Ia$_2$-3 contaminated with about 5% 1-methylnaphthalene. 81% of the ligand Ia$_2$-3 could thus be recovered by simple crystallization. A further 3.1 g of the ligand Ia$_2$-3 could be obtained in pure form by distilling off 1-methylnaphthalene.

TABLE 17

| Time in h | Citronellal added in g | Citronellal in % by wt. | Citronellal in g | Isopulegol in % by wt. | Isopulegol in g | Citronellol in % by wt. | Citronellol in g |
|---|---|---|---|---|---|---|---|
| 4 | 3.38 | 1.85 | 1.74 | 3.31 | 3.12 | 0.00 | 0.00 |
| 5 | 6.77 | 2.97 | 2.90 | 3.90 | 3.81 | 0.00 | 0.00 |
| 6 | 10.15 | 3.65 | 3.69 | 5.37 | 5.43 | 0.03 | 0.03 |
| 7 | 10.15 | 1.81 | 1.83 | 7.01 | 7.08 | 0.03 | 0.03 |
| 24 | 10.15 | 0.02 | 0.02 | 9.70 | 9.79 | 0.06 | 0.06 |

EXAMPLE 16

(Not According to the Invention): Cyclization of Citronellal with a Catalyst of Ligand 45 with Triethylaluminum in the Presence of Acetic Acid with Partial Conversion

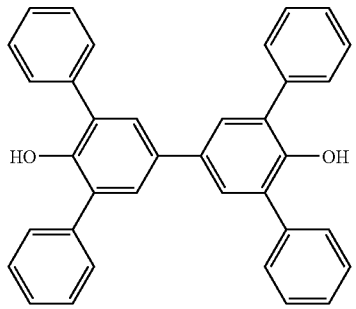

618 mg (1.2 mmol) of ligand 36 (purity: 98.8%) were dissolved in 30 g of toluene. 0.342 g (0.74 mmol) of triethylaluminum in the form of a 25% strength solution in toluene was slowly added. A gel-like product was formed and the mixture was after-stirred for a further 40 minutes at 20° C. The catalyst solution was then cooled to 0° C. and a solution of 11.7 g (74.4 mmol) of racemic citronellal and 61 my of acetic acid in 24 g of toluene was added in 6 portions. After each addition, the mixture was after-stirred for about 50 minutes. The reaction mixture was then stirred with 10 ml of 8% strength sodium hydroxide solution and the organic phase was separated off and analyzed by gas chromatography. The following results were obtained: citronellal: 63.9%; neo-isopulegol: 0.2%; isopulegol: 24.9%; neoiso-isopulegol: 0.1%; iso-isopulegol: 0.07%; citronellyl citronellate: 7.3%.

At a conversion of 34.1%, the selectivity for isopulegol was 74.2%. A product with the following isomer distribution (neo-isopulegol:isopulegol:neoiso-isopulegol:iso-isopulegol) was obtained: 0.8:98.5:0.4:0.3.

We claim:
1. A diarylphenoxyaluminum compound obtainable by reacting a bis(diarylphenol) ligand of the formula (I)

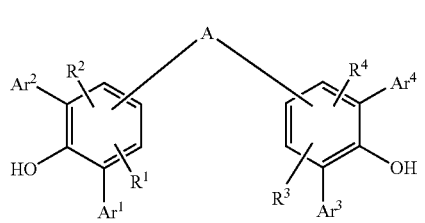

wherein $Ar^1$, $Ar^2$, $Ar^3$ and $Ar^4$ are identical or different and in each case, independently of one another, are an aryl radical having 6 to 15 carbon atoms or a heteroaryl radical having 2 to 15 carbon atoms which, optionally can in each case carry 1 to 7 identical or different substituents selected from the group of substituents $C_1$- to $C_6$-alkyl, $C_1$- to $C_6$-perfluoroalkyl, $C_1$- to $C_6$-alkoxy, $C_7$- to $C_{12}$-aralkyl, halogen, —$SiR^{5a}R^{6a}R^{7a}$, substituted or unsubstituted $C_6$- to $C_{10}$-aryl, —$NR^{8a}R^{9a}$, —$SR^{10}a$ or —$NO_2$, $R^1$, $R^2$, $R^3$ and $R^4$ are identical or different and in each case, independently of one another, are hydrogen, $C_1$- to $C_6$-alkyl, $C_1$- to $C_6$-perfluoroalkyl, $C_1$- to $C_6$-alkoxy, $C_7$- to $C_{12}$-aralkyl, halogen, —$SiR^{5b}R^{6b}R^{7b}$, substituted or unsubstituted $C_6$- to $C_{10}$-aryl, —$NR^{8b}R_{9b}$, —$SR^{10b}$, —$NO_2$, and $R^1$ or $R^2$ and/or $R^3$ or $R^4$, together with A, can form a cyclic aromatic or nonaromatic cycle, and A is A(1), A(2) or A(3), A(1) is a straight-chain or branched and/or cyclic hydrocarbon radical having 1 to 25 carbon atoms which is optionally saturated or mono- or polyunsaturated and/or partially aromatic and optionally can have one or more identical or different hetero atoms selected from the group consisting of hetero atoms O, S and $NR^{11}$, and/or one or more identical or different functional groups selected from the group consisting of functional groups C(O), S(O) and S(O)$_2$, and, optionally can carry one or more identical or different substituents selected from substituents $C_1$- to $C_6$-alkyl, $C_1$- to $C_6$-perfluoroalkyl, $C_1$- to $C_6$-alloxy, $C_1$- to $C_{10}$-acyloxy, $C_7$- to $C_{12}$-aralkyl, halogen, —$SiR^{5c}R^{6c}R^{7c}$, substituted or unsubstituted $C_6$- to $C_{10}$-aryl, substituted or unsubstituted $C_2$- to $C_{10}$-hetaryl, —$NR^{8c}R^{9c}$, —$SR^{10c}$, —$NO_2$, $C_1$-to $C_{12}$-acyl, or $C_1$- to $C_{10}$-carboxyl, A(2) is an aryl radical having 6 to 15 carbon atoms or a heteroaryl radical having 2 to 15 carbon atoms which, optionally can in each case carry 1 to 5 substituents, selected from the group of substituents $C_1$- to $C_6$-alkyl, $C_1$- to $C_6$-perfluoroalkyl, $C_1$- to $C_6$-alkoxy, $C_7$- to $C_{12}$-aralkyl, halogen, —$SiR^{5d}R^{6d}R^{7d}$, substituted or unsubstituted $C_6$- to $C_{10}$-aryl, —$NR^{8d}R^{9d}$, $SR^{10d}$ or $NO_2$, A(3) is a functional group or a hetero atom selected from the group consisting of —O—, —S—, —N($R^{11}$)—, —S(O)—, —C(O)—, S(O)$_2$—, —P($R^{11}$)$-^{(R11)}$P(O)— and Si($R^{12}R^{13}$), wherein the radicals $R^{5a}$, $R^{6a}$, $R^{7a}$, $R^{8a}$, $R^{9a}$, $R^{10a}$ to $R^{5d}$, $R^{6d}$, $R^{7d}$, $R^{8d}$, $R^{9d}$, $R^{10d}$ and $R^{11}$ to $R^{13}$ are in each case, independently of one another, $C_1$- to $C_6$-alkyl, $C_7$- to $C_{12}$-aralkyl and/or substituted or unsubstituted $C_6$- to $C_{10}$-aryl, and the radicals $R^{8a}$ and $R^{9a}$, $R^{8b}$ and $R^{9b}$, $R^{8c}$ and $R^{9c}$, $R^{8d}$ and $R^{9d}$, independently of one another, can in each case together also form a cyclic hydrocarbon radical having 2 to 8 carbon atoms which can have one or more identical or different hetero atoms selected from the group consisting of O, S and $NP^{11a}$ and $R^{11a}$ can have the meanings given for $R^{11}$, with an aluminum compound of the formula (II) or formula (III) or a mixture of compounds of the formulas (II) and (III)

$$(R^{14})_{3-p}AlH_p \qquad (II),$$

wherein

Al is aluminum and $R^{14}$ is a branched or unbranched alkyl radical having 1 to 5 carbon atoms and p is 0 or an integer from 1 to 3, $$MAlH_4 \qquad (III),$$

wherein

Al is aluminum and

M is lithium, sodium or potassium.

2. The diarylphenoxyaluminum compound according to claim 1, obtainable by reacting a bis(diarylphenol) ligand of the formula (Ia)

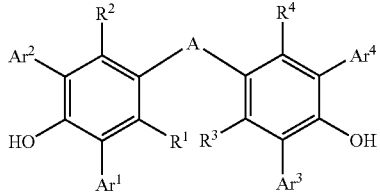

(Ia)

wherein the radicals $Ar^1$ to $Ar^4$, $R^1$ to $R^4$ and A have the meanings given in claim 1.

3. The diarylphenoxyaluminum compound according to claim 1, wherein the radicals $Ar^1$ to $Ar^4$ are phenyl.

4. The diarylphenoxyaluminum compound according to claim 1, wherein the radicals $R_1$ to $R_4$ are hydrogen.

5. The diarylphenoxyaluminum compound according to claim 1, wherein the bis(diarylphenol) ligand of the formula (I) and the aluminum compounds of the formulae (II) and/or (III) are used in a molar ratio of from 10:1 to 1:1.

6. The diarylphenoxyaluminum compound according to claim 1, wherein the bis(diarylphenol) ligand of the formula (I) and the aluminum compounds of the formulae (II) and/or (III) are used in a molar ratio of 3:2.

7. A method of producing isopulegol of the formula (IV)

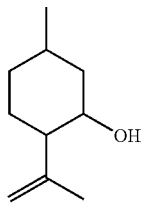

(IV)

comprising cyclization of a citronellal of the formula (V)

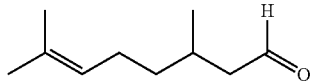

(V)

in the presence of a catalyst which is obtainable by reacting a bis(diarylphenol) ligand of the formula (I)

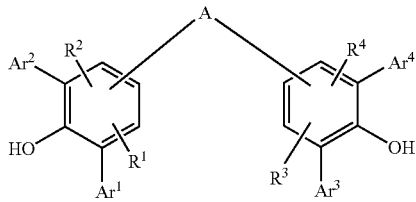

(I)

wherein
$Ar^1$, $Ar^2$, $Ar^3$ and $Ar^4$ are identical or different and in each case, independently of one another, are an aryl radical having 6 to 15 carbon atoms or a heteroaryl radical having 2 to 15 carbon atoms which, optionally can in each case carry 1 to 7 identical or different substituents selected from the group of substituents $C_1$- to $C_6$-alkyl, $C_1$- to $C_6$-perfluoroalkyl, $C_1$- to $C_6$-alkoxy, $C_7$- to $C_{12}$-aralkyl, halogen, —$SiR^{5a}R^{6a}R^{7a}$, substituted or unsubstituted $C_6$- to $C_{10}$-aryl, —$NR^{8a}R^{9a}$, —$SR^{10a}$ or —$NO_2$, $R^1$, $R^2$, $R^3$ and $R^4$ are identical or different and in each case, independently of one another, are hydrogen, $C_1$- to $C_6$-alkyl, $C_1$- to $C_6$-perfluoroalkyl, $C_1$- to $C_6$-alkoxy, $C_7$- to $C_{12}$-aralkyl, halogen, —$SiR^{5b}R^{6b}R^{7b}$, substituted or unsubstituted $C_6$- to $C_{10}$-aryl, —$NR^{8b}R^{9b}$, —$SR^{10b}$, —$NO_2$, and $R^1$ or $R^2$ and/or $R^3$ or $R^4$, together with A, can form a cyclic aromatic or nonaromatic cycle, and A is A(1), A(2) or A(3), A(1) is a straight-chain or branched and/or cyclic hydrocarbon radical having 1 to 25 carbon atoms which is optionally saturated or mono- or polyunsaturated and/or partially aromatic and optionally can have one or more identical or different hetero atoms selected from the group consisting of hetero atoms O, S and $NR^{11}$, and/or one or more identical or different functional groups selected from the group consisting of functional groups C(O), S(O) and $S(O)_2$, and, optionally can carry one or more identical or different substituents selected from substituents $C_1$- to $C_6$-alkyl, $C_1$- to $C_6$-perfluoroalkyl, $C_1$- to $C_6$-alkoxy, $C_1$- to $C_{10}$-acyloxy, $C_7$- to $C_{12}$-aralkyl, halogen, —$SiR^{5c}R^{6c}R^{7c}$, substituted or unsubstituted $C_6$- to $C_{10}$-aryl, substituted or unsubstituted $C_2$- to $C_{10}$-hetaryl, —$NR^{8c}R^{9c}$, —$SR^{10c}$, —$NO_2$, $C_1$-to $C_{12}$-acyl, or $C_1$- to $C_{10}$-carboxyl, A(2) is an aryl radical having 6 to 15 carbon atoms or a heteroaryl radical having 2 to 15 carbon atoms which, optionally can in each case carry 1 to 5 substituents, selected from the group of substituents $C_1$- to $C_6$-alkyl, $C_1$- to $C_6$-perfluoroalkyl, $C_1$- to $C_6$-alkoxy, $C_7$- to $C_{12}$-aralkyl, halogen, —$SiR^{5d}R^{6d}R^{7d}$, substituted or unsubstituted $C_6$- to $C_{10}$-aryl, —$NR^{8d}R^{9d}$, $SR^{10d}$ or $NO_2$, A(3) is a functional group or a hetero atom selected from the group consisting of —O—, —S—, —$N(R^{11})$—, —S(O)—, —C(O)—, —$S(O)_2$—, —$P(R^{11})$—, —$(R^{11})$P(O)— and —$Si(R^{12}R^{13})$, wherein the radicals $R^{5a}$, $R^{6a}$, $R^{7a}$, $R^{8a}$, $R^{9a}$, $R^{10a}$ to $R^{5d}$, $R^{6d}$, $R^{7d}$, $R^{8d}$, $R^{9d}$, $R^{10d}$ and $R^{11}$ to $R^{13}$ are in each case, independently of one another, $C_1$- to $C_6$-alkyl, $C_7$- to $C_{12}$-aralkyl and/or substituted or unsubstituted $C_6$- to $C_{10}$-aryl, and the radicals $R^{8a}$ and $R^{9a}$, $R^{8b}$ and $R^{9b}$, $R^{8c}$ and $R^{9c}$, $R^{8d}$ and $R^{9d}$, independently of one another, can in each case together also form a cyclic hydrocarbon radical having 2 to 8 carbon atoms which can have one or more identical or different hetero atoms selected from the group consisting of O, S and $NR^{11a}$ and $R^{11a}$ can have the meanings given for $R^{11}$, with an aluminum compound of the formula (II) or formula (III) or a mixture of compounds of the formulas (II) and (III), $$(R^{14})_{3-p}AlH_p \qquad (II),$$

wherein

Al is aluminum and $R^{14}$ is a branched or unbranched alkyl radical having 1 to 5 carbon atoms and p is 0 or an integer from 1 to 3, $$MAlH_4 \qquad (III),$$

wherein
Al is aluminum and
M is lithium, sodium or potassium.

8. The method according to claim 7, wherein the cyclization is carried out in the presence of a catalyst which is obtainable by reacting a bis(diarylphenol) ligand of the formula (Ia)

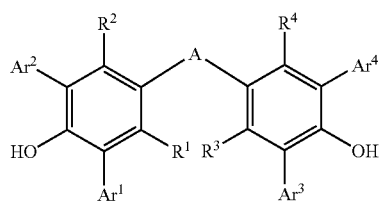

(Ia)

wherein
Ar$^1$, Ar$^2$, Ar$^3$, Ar$^4$, R$^1$, R$^2$, R$^3$, R$^4$ and A are defined in claim 7.

9. The method according to claim 7 for producing optically active isopulegol of the formula (IVa)

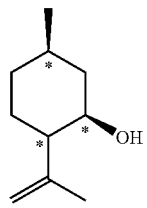

(IVa)

comprising the cyclization of optically active citronellal of the formula (Va)

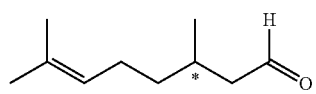

(Va)

wherein (*) refers in each case to an asymmetric carbon atom.

10. The method according to claim 7 for producing L-(−)-isopulegol comprising the cyclization of D-(+)-citronellal and the aluminum compound used is a compound of the formula (II).

11. The method according to claim 7, wherein the aluminum compound used is trimethylaluminum or triethylaluminum.

12. The method according to claim 7, wherein the bis (diarylphenol) ligand of the formula (I) and the aluminum compounds of the formulae (II) and/or (III) are used in a molar ratio of from 10:1 to 1:1.

13. The method according to claim 7, wherein the bis (diarylphenol) ligand of the formula (I) and the aluminum compounds of the formulae (II) and/or (III) are used in a molar ratio of 1.5:1.

14. The method according to claim 7, wherein the cyclization is carried out in the presence of an organic acid.

15. The method according to claim 14, wherein the organic acid used is acetic acid.

16. The method according to claim 7, wherein the cyclization is carried out in the presence of at least one compound selected from the group of carboxylic acid anhydrides, aldehydes, ketones and vinyl ethers.

17. The method according to claim 16, wherein the cyclization is carried out in the presence of a carboxylic acid anhydride of the formula (VI)

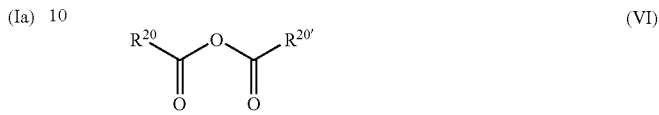

(VI)

wherein
R$^{20}$ and R$^{20'}$ are identical or different and are a branched or unbranched C$_1$- to C$_{12}$-alkyl radical or C$_7$- to C$_{12}$-aralkyl radical or a C$_6$- to C$_{10}$-aryl radical, wherein the specified radicals can in each case have one or more identical or different substituents selected from the group consisting of OR$^{10e}$, SR$^{10e}$, NR$^{8e}$R$^{9e}$ and halogen and wherein R$^{20}$ and R$^{20'}$ can together also form a 5- to 8-membered ring which can have one or more ethylenic double bonds and one or more identical or different hetero atoms selected from the group consisting of O, S and NR$^{11b}$ and wherein R$^{10e}$, R$^{10f}$, R$^{8e}$, R$^{9e}$ and R$^{11b}$, independently of one another, can have the meanings given for R$^{11}$, or in the presence of an aldehyde of the formula (VII)

(VII)

wherein
R$^{21}$ is a branched or unbranched C$_1$- to C$_{12}$-alkyl radical or C$_7$- to C$_{12}$-aralkyl radical or a C$_6$- to C$_{10}$-aryl radical, wherein the specified radicals can in each case have one or more identical or different substituents selected from the group consisting of OR$^{10e}$, SR$^{10f}$ and NR$^{8e}$R$^{9e}$ and halogen, wherein R$^{10e}$, R$^{10f}$, R$^{8e}$ and R$^{9e}$, independently of one another, can have the meanings given for R$^{11}$, or in the presence of a ketone of the formula (VIII)

(VIII)

wherein
R$^{22}$ and R$^{23}$ are identical or different and are in each case a branched or unbranched C$_1$- to C$_{12}$-alkyl radical or C$_7$- to C$_{12}$-aralkyl radical or a C$_6$- to C$_{10}$-aryl radical or a C$_1$- to C$_6$-alkoxycarbonyl radical, wherein the specified radicals can in each case have one or more identical or different substituents selected from the group consisting of OR$^{10e}$, SR$^{10f}$, NR$^{8e}$R$^{9e}$ and halogen, and wherein R$^{22}$ and R$^{23}$ can together also form a 5- to 8-membered ring which has one or more ethylenic double bonds and one or more identical or different hetero atoms selected from the group consisting of O, S and NR$^{11b}$, and wherein $R^{10e}$, $R^{10f}$, $R^{8e}$, $R^{9e}$ and $R^{11b}$, independently of one another, can have the meanings given for $R^{11}$, or in the presence of a vinyl ether of the general formula (IX)

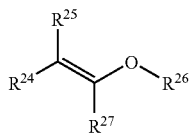

(IX)

wherein $R^{24}$, $R^{25}$, $R^{26}$ and $R^{27}$ are identical or different and, independently of one another, are in each case a branched or unbranched $C_1$- to $C_{12}$-alkyl radical or $C_7$- to $C_{12}$-aralkyl radical or a $C_6$- to $C_{10}$-aryl radical, wherein the specified radicals can in each case have one or more identical or different substituents selected from the group consisting of oxo, $OR^{10e}$, $SR^{10f}$, $NR^{8e}R^{9e}$ and halogen and wherein $R^{25}$ and $R^{26}$ can together also form a 5- to 8-membered ring which can have one or more ethylenic double bonds and one or more identical or different hetero atoms selected from the group consisting of O, S and $NR^{11b}$ and wherein $R^{10e}$, $R^{10f}$, $R^{8e}$, $R^{9e}$ and $R^{11b}$, independently of one another, can have the meanings given for $R^{11}$.

18. The method according to claim 16, wherein the cyclization is carried out in the presence of acetaldehyde, propionaldehyde, chloral, 1,1,1-trifluoroacetone, 1,1,1-trifluoroacetophenone, methyl pyruvate, ethyl pyruvate or hexafluoroacetone.

19. The method according to claim 16, wherein the carboxylic anhydride, the aldehyde, the ketone and/or the vinyl ether is used in an amount of from 0.01 mol % to 5 mol %, based on the amount of citronellal used.

20. The method according to claim 16, wherein a solution or suspension of the catalyst is initially introduced and a mixture of the citronellal to be reacted with the carboxylic acid anhydride, the aldehyde, the ketone and/or the vinyl ether is added.

21. The method according to claim 20, wherein the mixture of the citronellal to be reacted with the carboxylic acid anhydride, the aldehyde, the ketone and/or the vinyl ether is added within a period of from 30 minutes to 6 hours.

22. The method according to claim 11, wherein the bis (diarylphenol) ligand of the formula (I) and the diarylphenoxy-aluminum compound used as catalyst used is recovered after the reaction has taken place.

23. The method according to claim 7, comprising the steps
 a) optionally distillative removal of the solvent used, and optionally the further compound used from the product mixture,
 b) addition of a high-boiling solvent to the residue obtained in step a),
 c) distillative separation of the isopulegol from the mixture obtained in step b) and
 d) cooling of the distillation bottom obtained in step c) with crystallization of the bis(diarylphenol) ligand of the formula (I) used.

24. A method of producing menthol comprising the production of isopulegol of the formula (IV) according to claim 7 and subsequent hydrogenation of the ethylenic double bond of the isopulegol obtained in this way.

25. The method according to claim 24 of producing optically active menthol comprising the steps
 a) production of optically active isopulegol of the formula (IVa) according to claim 7 and
 b) hydrogenation of the ethylenic double bond of the optically active isopulegol obtained in this way.

* * * * *